(12) United States Patent
Saito et al.

(10) Patent No.: US 10,156,304 B2
(45) Date of Patent: Dec. 18, 2018

(54) FLEXIBLE TUBE AND INSERTION DEVICE

(71) Applicant: OLYMPUS CORPORATION, Hachioji-shi, Tokyo (JP)

(72) Inventors: Kenichiro Saito, Tachikawa (JP); Takahiro Kishi, Yokohama (JP); Naoyuki Hoshi, Aizuwakamatsu (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/602,556

(22) Filed: May 23, 2017

(65) Prior Publication Data
US 2017/0254447 A1 Sep. 7, 2017

Related U.S. Application Data

(63) Continuation of application No. PCT/JP2015/083799, filed on Dec. 1, 2015.

(30) Foreign Application Priority Data

Dec. 2, 2014 (JP) .................................. 2014-244357

(51) Int. Cl.
*A61B 1/00* (2006.01)
*F16L 11/10* (2006.01)
(Continued)

(52) U.S. Cl.
CPC ................ *F16L 11/10* (2013.01); *A61B 1/00* (2013.01); *A61B 1/0055* (2013.01);
(Continued)

(58) Field of Classification Search
CPC ........... A61B 1/00064; A61B 1/00078; A61M 25/0053; A61M 25/0054; A61M 25/0147;
(Continued)

(56) References Cited

U.S. PATENT DOCUMENTS 5,549,542 A * 8/1996 Kovalcheck ......... A61B 1/0052
600/146
2009/0023989 A1* 1/2009 Honda ............... A61B 1/00133
600/106
(Continued)

FOREIGN PATENT DOCUMENTS

JP S58-103431 A 6/1983
JP H07-213481 A 8/1995
(Continued)

OTHER PUBLICATIONS

Feb. 23, 2016 Search Report issued in International Patent Application No. PCT/JP2015/083799.
(Continued)

*Primary Examiner* — Timothy J Neal
*Assistant Examiner* — Aaron B Fairchild
(74) *Attorney, Agent, or Firm* — Oliff PLC

(57) ABSTRACT

A flexible tube includes an envelope, a spiral tube and a built-in component. The spiral tube includes a first area portion and a second area portion. The spiral tube is under an initial tension throughout the overall length, and the built-in component includes a supplement area portion which supplements the elasticity of the spiral tube.

11 Claims, 10 Drawing Sheets

(51) Int. Cl.
  *A61B 1/005*  (2006.01)
  *F16L 11/16*  (2006.01)
  *A61M 25/00*  (2006.01)
  *G02B 23/24*  (2006.01)
  *A61B 17/00*  (2006.01)

(52) U.S. Cl.
  CPC ..... *A61B 1/00078* (2013.01); *A61M 25/0053* (2013.01); *F16L 11/16* (2013.01); *G02B 23/2476* (2013.01); *A61B 2017/00305* (2013.01)

(58) Field of Classification Search
  CPC ...... F16L 11/081; F16L 11/082; F16L 11/083; F16L 11/10; F16L 11/16
  See application file for complete search history.

(56) References Cited

U.S. PATENT DOCUMENTS

| | | | | |
|---|---|---|---|---|
| 2010/0280449 | A1* | 11/2010 | Alvarez | A61B 1/0055 604/95.04 |
| 2013/0112457 | A1* | 5/2013 | Kitagawa | A61B 1/0056 174/68.3 |
| 2013/0144126 | A1* | 6/2013 | Iede | A61B 1/0055 600/139 |
| 2014/0155697 | A1 | 6/2014 | Iede | |

FOREIGN PATENT DOCUMENTS

| JP | H08-313820 A | 11/1996 |
|---|---|---|
| JP | H08-327915 A | 12/1996 |
| JP | H11-262470 A | 9/1999 |
| JP | 2008-229067 A | 10/2008 |
| JP | 2012-509783 A | 4/2012 |
| JP | 2013-097327 A | 5/2013 |
| JP | 2014-113320 A | 6/2014 |

OTHER PUBLICATIONS

Oct. 4, 2016 Office Action issued in Japanese Patent Application No. 2016-553677.

Jun. 6, 2017 Preliminary Report on Patentability issued in International Patent Application No. PCT/JP2015/083799.

* cited by examiner

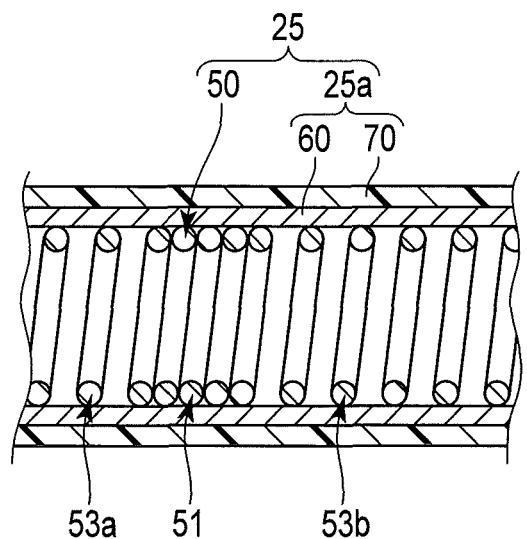
F I G. 3B
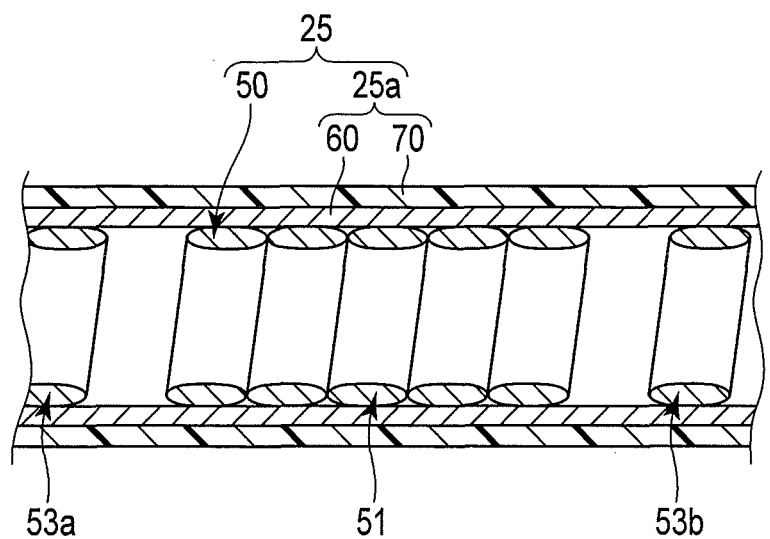
F I G. 3C

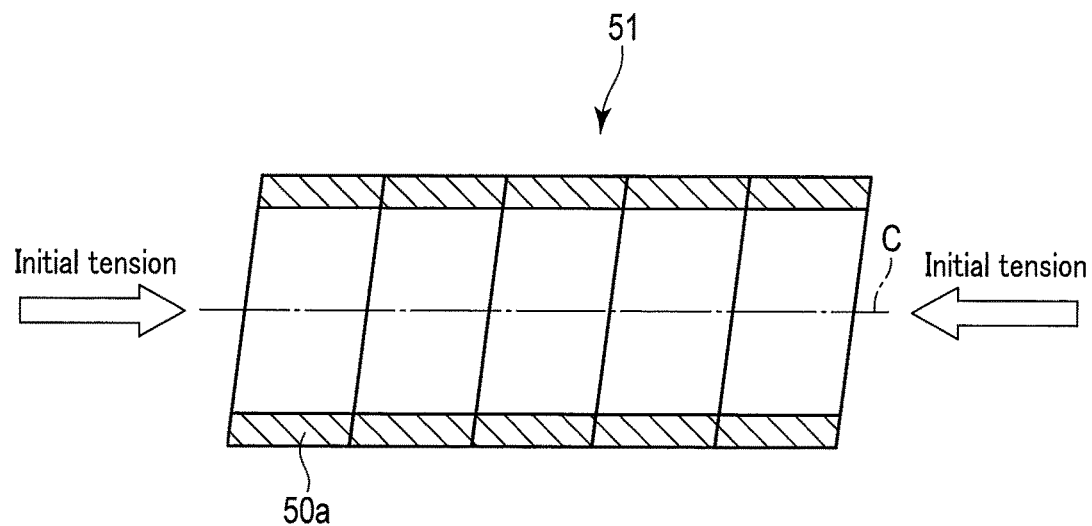
F I G. 4A
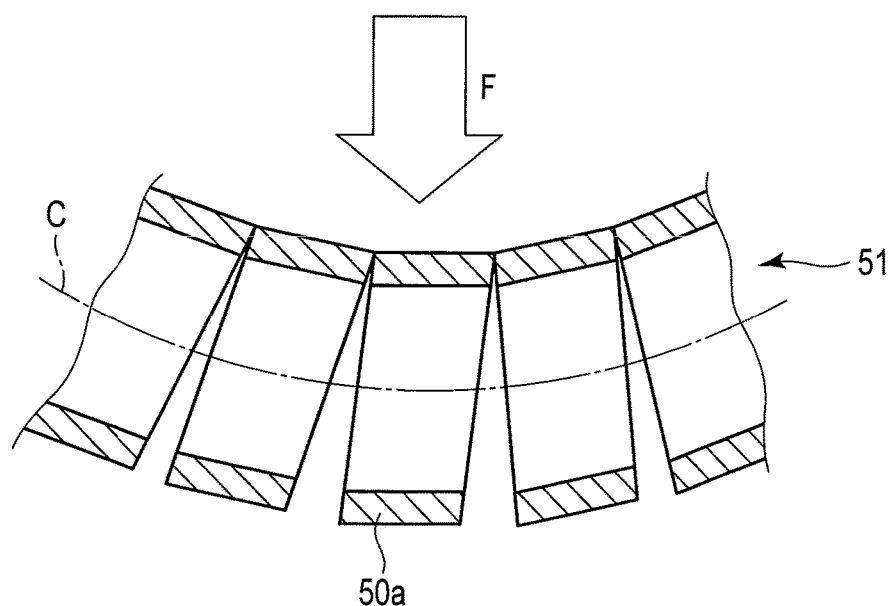
F I G. 4B

L4=L1+L2+L3

L5=L1+ΔT1+L2−ΔT2+L3−ΔT3
L4=L5
ΔT1=ΔT2+ΔT3

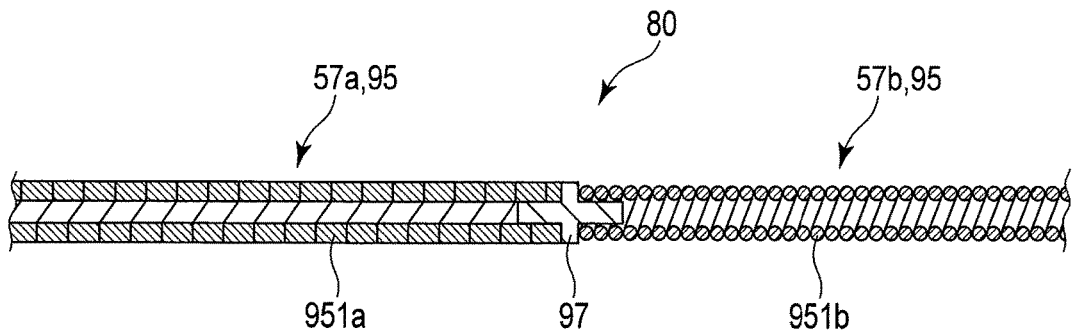
F I G. 7B
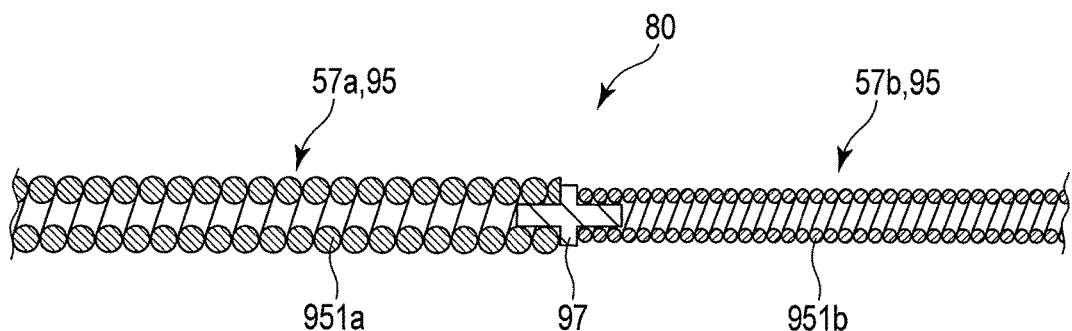
F I G. 7C
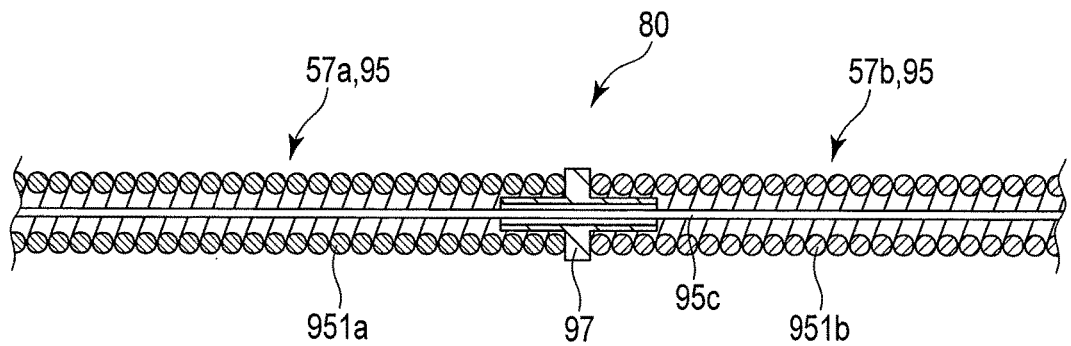
F I G. 7D

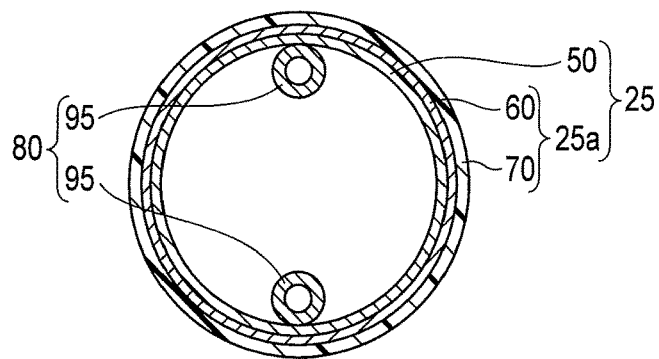
F I G. 9A
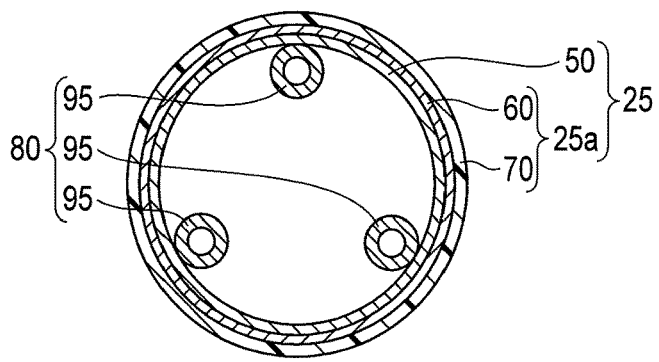
F I G. 9B
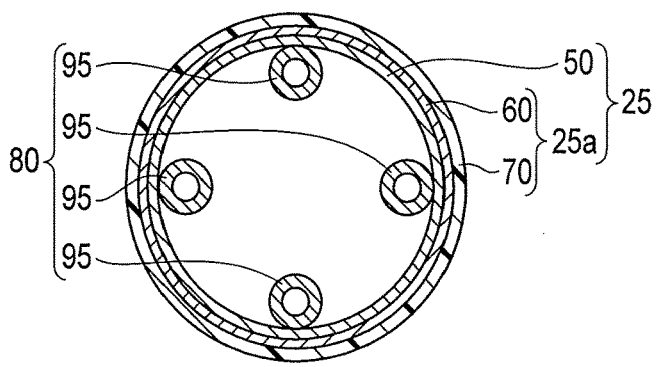
F I G. 9C though the example, the present invention, a flexible tube and insertion device.

FLEXIBLE TUBE AND INSERTION DEVICE

CROSS-REFERENCE TO RELATED APPLICATIONS

This application is a Continuation Application of PCT Application No. PCT/JP2015/083799, filed Dec. 1, 2015 and based upon and claiming the benefit of priority from prior Japanese Patent Application No. 2014-244357, filed Dec. 2, 2014, the entire contents of all of which are incorporated herein by reference.

BACKGROUND OF THE INVENTION

1. Field of the Invention

The present invention relates to a flexible tube which is used in an insertion portion of an insertion device inserted into a tube or the like, and which includes a spiral tube, and also to an insertion device having the flexible tube.

2. Description of the Related Art

For example, Jpn. Pat. Appln. KOKAI Publication No. 08-313820 discloses a flexible tube for use in an endoscope serving as an insertion device. The flexible tube includes a double spiral tube, a reticular body covering the double spiral tube, and an envelope layer covering the reticular body. The double spiral tube includes an inner spiral tube located on the inner side, and an outer spiral tube located on the outer side.

Each of the inner spiral tube and the outer spiral tube is spirally wound at constant pitches. A winding direction of the inner spiral tube is opposite to that of the outer spiral tube. At least one of an end portion of the inner spiral tube and an end portion of the outer spiral tube is formed as a densely wound portion.

For example, Jpn. Pat. Appln. KOKAI Publication No. 11-262470 discloses an insertion portion for use in an endoscope serving as an insertion device. A flexible tube of the insertion portion includes a spiral tube, a reticular body covering the spiral tube, and an envelope covering the reticular body. A wire guide is inserted through the flexible tube. The wire guide guides an operation wire inserted therethrough. The wire guide is made of a coil pipe, and the coil pipe is formed by densely winding a stainless steel wire such that the resultant winding has a constant diameter.

The wire guide is inserted into a flexibility-suppressing coil pipe (hereinafter referred to simply as a pipe). The pipe extends from a proximal end of the flexible tube to an intermediate point of the flexible tube. The pipe is formed by winding, like a coil, a thin metal wire, e.g., a stainless steel wire, such that the resultant winding has a constant diameter. In a distal end portion of the pipe, the winding pitch gradually increases in the direction toward the distal end, and the winding of the distal end portion becomes looser in that direction. With this structure, the flexibility changes smoothly at the intermediate point of the flexible tube.

For example, Jpn. Pat. Appln. KOKAI Publication No. 08-327915 discloses a flexible tube for use in an endoscope serving as an insertion device. The flexible tube includes a double spiral tube, a reticular body covering the double spiral tube, and an envelope layer covering the reticular body. The double spiral tube includes an inner spiral tube located on the inner side, and an outer spiral tube located on the outer side.

Each of the inner spiral tube and the outer spiral tube is spirally wound at constant pitches. A winding direction of the inner spiral tube is opposite to that of the outer spiral tube. A plate member forming the outer spiral tube is comparatively wide at a proximal end side and is comparatively narrow at a distal end side. With this structure, the flexible tube has high flexibility in a distal end side and has high rigidity in a proximal end side.

BRIEF SUMMARY OF THE INVENTION

According to one aspect of the present invention, a flexible tube for use in an insertion device is provided. The flexible tube comprises a flexible envelope which includes at least one layer arranged in a radial direction of the flexible tube; a spiral tube including (i) a first area portion which includes a densely wound portion under an initial tension, and a loosely wound portion continuous with at least one end of the densely wound portion, the densely wound portion and the loosely wound portion being alternately arranged in a direction of a central axis of the spiral tube, and (ii) a second area portion which is continuous with the first area portion and includes a loosely wound portion similar to the loosely wound portion of the first area portion, the spiral tube being covered with the envelope and providing elasticity in cooperation with the envelope; a built-in component which is contained in the spiral tube, and including a supplement area portion that is under the initial tension throughout overall length thereof, and supplements the elasticity of the spiral tube.

According to another aspect of the present invention, an insertion device is provided. The insertion device comprises an insertion portion configured to be inserted into a lumen, and the insertion portion has such a structure as describe above.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3B is a longitudinal sectional view of the three-layered structure of the flexible tube and illustrates a state where the thin plate member of the spiral tube has a circular cross section.

FIG. 3C is a longitudinal sectional view of the three-layered structure of the flexible tube and illustrates a state where the thin plate member of the spiral tube has an elliptical cross section.

FIG. 4A is a schematic longitudinal sectional view illustrating a state where a densely wound portion of the flexible tube is under an initial tension acting in the central axis direction and maintains a straight state.

FIG. 4B is a schematic longitudinal sectional view illustrating a state where the densely wound portion is applied with an external force sideways with reference to the central axis thereof and is deformed.

FIG. 7B illustrates the structure of a built-in densely wound member of the first modification of the second embodiment.

FIG. 7C illustrates the structure of a built-in densely wound member of the second modification of the second embodiment.

FIG. 7D illustrates the structure of a built-in densely wound member of the third modification of the second embodiment.

FIG. 9A illustrates an example of how the built-in densely wound member of the fourth embodiment is arranged.

FIG. 9B illustrates another example of how the built-in densely wound member of the fourth embodiment is arranged.

FIG. 9C illustrates still another example of how the built-in densely wound member of the fourth embodiment is arranged.

DETAILED DESCRIPTION OF EMBODIMENTS

Hereinafter, embodiments of the present invention will be described with reference to the accompanying drawings.

A description will be given of the case where an insertion device of the embodiment is a medical endoscope 10. The insertion device may be suitably realized as not only the medical endoscope 10 but also an industrial endoscope, or an insertion device having neither illumination optical system nor observation optical system. This type of insertion device is, for example, a catheter.

First Embodiment

[Configuration]

The first embodiment will be described with reference to FIGS. 1, 2A, 2B, 3A, 3B, 3C, 4A, 4B, 5A and 5B.

Figure 2A:
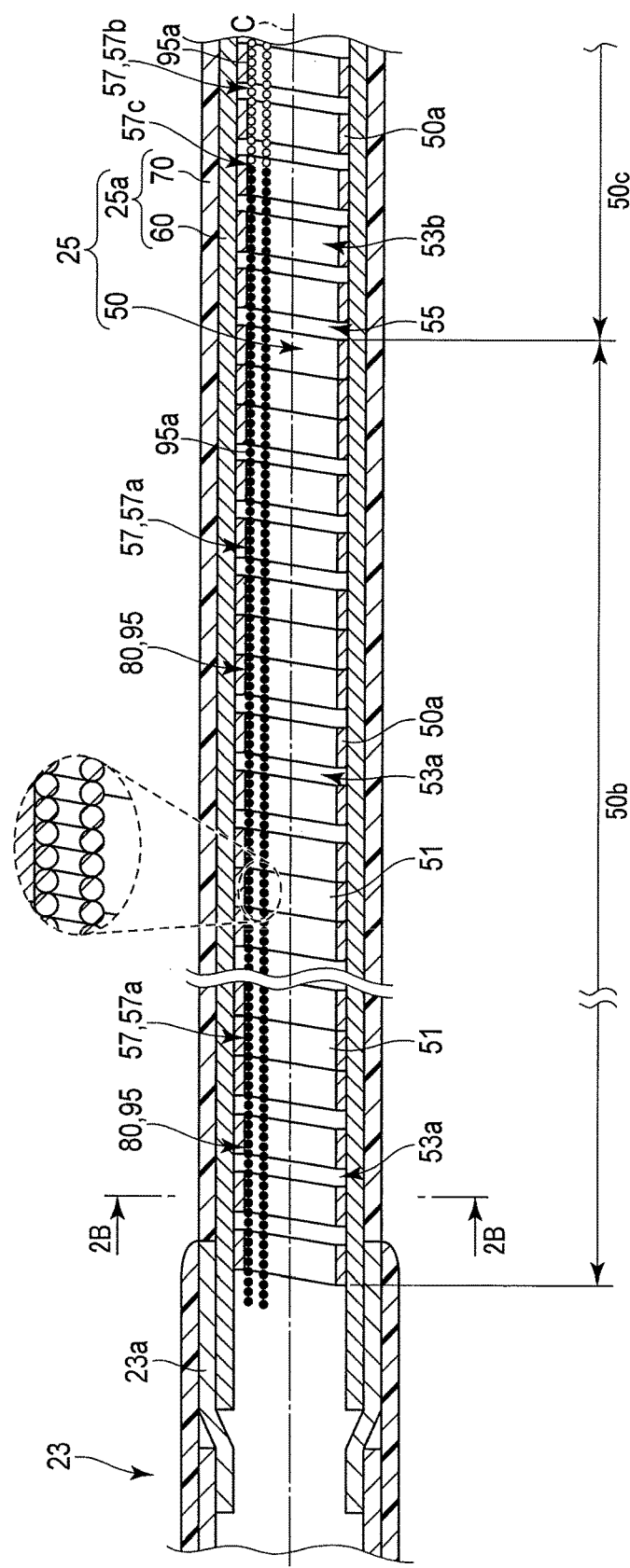
FIG. 2A is a schematic longitudinal sectional view showing the three-layered structure of a flexible tube, schematically illustrates an internal structure of the flexible tube, illustrates a built-in densely wound member of the first embodiment, and illustrates positional relationships among a first area portion, a second area portion and a supplement area portion.

In some of the Figures, illustration of some structural elements is omitted for the sake of easy understanding of the structure. For example, in FIG. 2A, illustration of an illumination cable 81, an image cable 83, a gas sending/water sending tube 85, a channel 87, a bending wire 91 and a wire insertion member 93 is omitted.

To make clear distinction between a first supplement area portion 57a and a second supplement area portion 57b in the drawings, they are indicated in different ways in the drawings. For example, in the built-in densely wound member 95 depicted in FIG. 2A, the first supplement area portion 57a is indicated by black circles, and the second supplemental area portion 57b is indicated by white circles.

[Endoscope 10]

Figure 1:
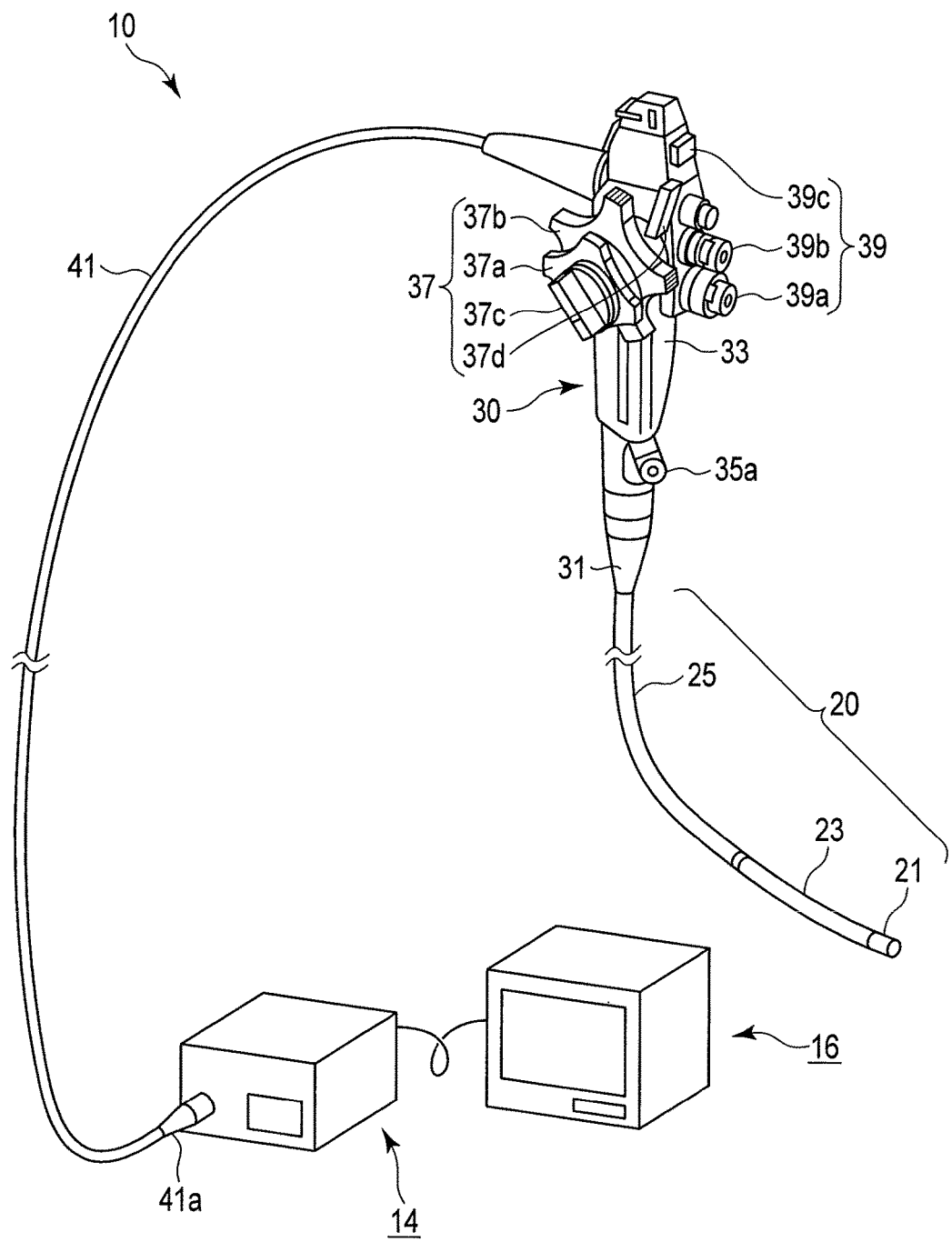
FIG. 1 is a schematic diagram showing an endoscope according to the present invention.

As shown in FIG. 1, the endoscope 10 comprises: a hollow elongated insertion portion 20 to be inserted into a lumen (e.g., a body cavity); and an operation portion 30 coupled to a proximal end portion of the insertion portion 20 and configured to operate the endoscope 10.

[Insertion Portion 20]

The insertion portion 20 includes, from its distal end portion side to its proximal end portion side, a distal end hard portion 21, a bendable portion 23 and a flexible tube 25. A proximal end portion of the distal end hard portion 21 is coupled to a distal end portion of the bendable portion 23, and a proximal end portion of the bendable portion 23 is coupled to a distal end portion of the flexible tube 25. The distal end hard portion 21, the bendable portion 23 and the flexible tube 25 are arranged along a central axis C of the insertion portion 20.

The distal end hard portion 21 is the distal end portion of the insertion portion 20. It is hard and cannot be bent. The distal end hard portion 21 includes a main body portion (not shown) made, for example, of stainless steel, and an envelope portion (not shown) covering an outer periphery of the main body portion. The main body portion is, for example, hard and cylindrical. The envelope portion is tubular and insulative. The distal ends of built-in components 80 (FIG. 2B), described later, are fixed inside the main body portion.

The bendable portion 23 can be bent in any direction desired (e.g., in the upward/downward direction and rightward/leftward direction) in response to an operation of a bending operation portion 37 mentioned later. The position and direction of the distal end hard portion 21 are changed by a bending operation of the bendable portion 23. Illumination light (not shown) is radiated to an observation target, and the observation target is caught within an observation field. The observation target is, for example, an affected portion and a disease portion of a subject (e.g., a portion of the body cavity).

The flexible tube 25 has desirable flexibility and can be bent when an external force F is applied thereto. The external force F is, for example, a force applied to the flexible tube 25 at an angle to the central axis C of the flexible tube (i.e., the central axis C of the insertion portion 20). The flexible tube 25 is a tubular member extended from a main body portion 31 (described later) of the operation portion 30. The structure of the flexible tube 25 will be described later.

[Operation Portion 30]

The operation portion 30 includes the main body portion 31 from which the flexible tube 25 extends, a grasping portion 33 coupled to a proximal end portion of the main body portion 31 and grasped by an operator who operates the endoscope 10, and a universal cord 41 extending from the grasping portion 33.

[Main Body Portion 31]

The main body portion 31 has a treatment instrument insertion port 35a. The treatment instrument insertion port 35a is coupled to a proximal end portion of a treatment instrument insertion channel (hereinafter referred to as a channel 87 (see FIG. 2B)). The channel 87 is arranged inside the insertion portion 20 and extends from the treatment instrument insertion port 35a to the distal end hard portion 21 through the flexible tube 25 and the bendable portion 23. A distal end portion of the channel 87 communicates with a distal end opening portion (not shown) of the distal end hard portion 21. The treatment instrument insertion port 35a is a port from which an endoscope treatment instrument (hereinafter referred to as treatment instrument) (not shown) is inserted into the channel 87. The treatment instrument is inserted into the channel 87 from the treatment instrument insertion port 35a and is pushed toward the distal end hard portion 21. The treatment insertion is projected from the distal end opening portion.

[Grasping Portion 33]

The grasping portion 33 includes the bending operation portion 37 with which the bendable portion 23 is bent and a switch portion 39.

[Bending Operation Portion 37]

Figure 2B:
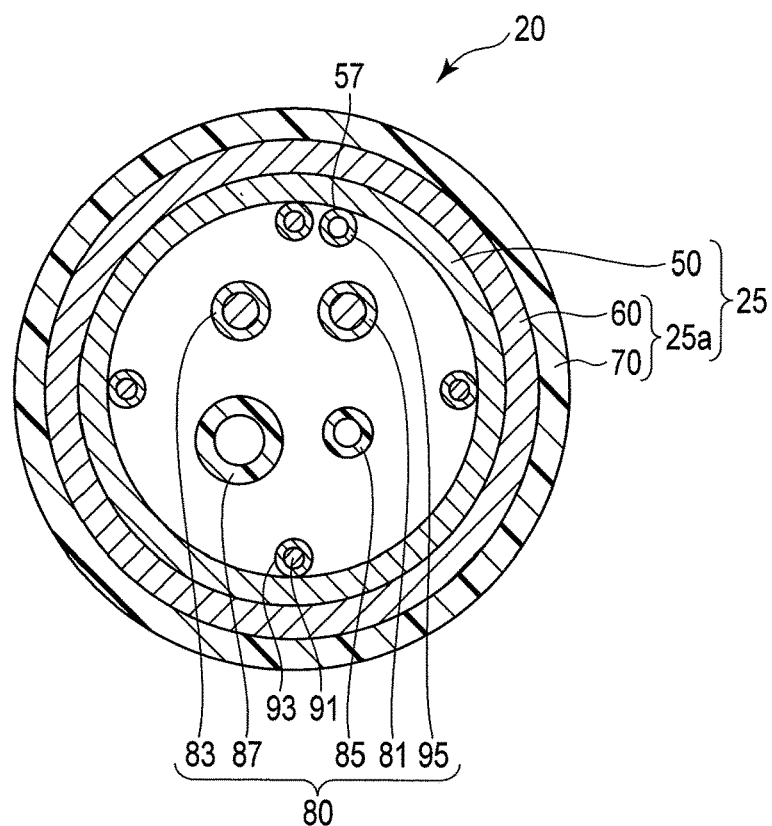
FIG. 2B is a sectional view taken along line 2B-2B shown in FIG. 2A.

The bending operation portion 37 includes a right/left bending operation knob 37a, which is for bending the bendable portion 23 rightward or leftward by means of right/left bending wires 92 (FIG. 2B), and an up/down bending operation knob 37b, which is for bending the bendable portion 23 upward or downward by means of up/down bending wire 92 (FIG. 2B). The bending operation portion 37 also includes a right/left fixing know 37c, which is for fixing the bendable portion 23 in a horizontally bent state, and an up/down fixing knob 37d, which is for fixing the bendable portion 23 in a vertically bent state.

[Switch Portion 39]

The switch portion 39 includes a gas sending/water sending switch 39a, a suction switch 39b, and various switches 39c for endoscopic imaging. The gas sending/water sending switch 39a, the suction switch 39b, and the switches 39c are operated by the operator, with the grasping portion 33 being grasped by the operator.

The gas sending/water sending switch 39a is operated when a gaseous fluid is supplied from a gas sending tube (not shown) and the gas sending/water sending tube 85 (shown in FIG. 2B) and when a liquid fluid is supplied from a water tube (not shown) and the gas sending/water sending tube (shown in FIG. 2B), so as to ensure a field of observation of an imaging unit (not shown) at the distal end hard portion 21. The fluid includes water and a gas.

The suction switch 39b is operated when the endoscope 10 sucks a fluid including mucus from the distal end opening portion, which functions as a suction opening portion as well, by way of the channel 87 which functions as a suction channel as well.

Inside the endoscope 10, the gas sending tube, the water sending tube and the gas sending/water sending tube are extended from the insertion portion 20 to the universal cord 41 by way of the main body portion 31 and the grasping portion 33.

[Universal Cord 41]

The universal cord 41 includes a connector 41a detachably attached to a control device 14. The control device 14 controls the endoscope 10. The control device 14 includes an image processor (not shown) for processing the images taken by the imaging unit. The control device 14 is connected to a monitor 16, which is a display device for displaying the images taken by the imaging unit.

[Structure of Flexible Tube 25]

As shown in FIGS. 2A and 2B, the flexible tube 25 has a hollow shape, for example. The flexible tube 25 includes, for example, a spiral tube 50 containing built-in components 80, a reticular tube 60 being in contact with an outer circumferential surface of the spiral tube 50 and covering that outer circumferential surface of the spiral tube 50, and an envelope portion 70 being in contact with an outer circumferential surface of the reticular tube 60 and covering that outer circumferential surface of the reticular tube 60. The reticular tube 60 is stacked on the outer circumferential surface of the spiral tube 50, and the envelope portion 70 is stacked on the outer circumferential surface of the reticular tube 60.

As described, the flexible tube 25 is made up of the spiral tube 50, the reticular tube 60 and the envelope portion 70, and has a three-layered structure including these.

The reticular tube 60 can be omitted, if so desired. In other words, the flexible tube 25 may be made up of the spiral tube 50 and the envelope portion 70, and has a two-layered structure including these.

Accordingly, the flexible tube 25 may be made up of the spiral tube 50 and a cover portion being in contact with the outer circumferential surface of the spiral tube 50 and covering the outer circumferential surface of the spiral tube 50. The cover portion includes at least the envelope portion 70 described above. The cover portion functions as a flexible envelope 25a which includes at least one layer in a radial direction of the flexible tube 25. In the present embodiment, the envelope 25a includes the reticular tube 60 and the envelope portion 70.

[Spiral Tube 50]

The spiral tube 50 of the present embodiment is covered with the envelope 25a. The spiral tube 50 has desirable elasticity. In cooperation with the envelope 25a, this elasticity includes, for example, bouncing property, impact resilience, hysteresis, spring property, resilience and the like, and has property to return the bent spiral tube 50 back to a substantially straight state.

As shown in FIG. 2A, the spiral tube 50 is formed by spirally winding a band-like thin plate member 50a, and is formed like a coil pipe. That is, the spiral tube 50 is a spiral elastic tube having desired elasticity. The thin plate member 50a is a plate member which has a rectangular shape and which is long and thin. The thin plate member 50a is made, for example, of stainless steel.

Figure 3A:
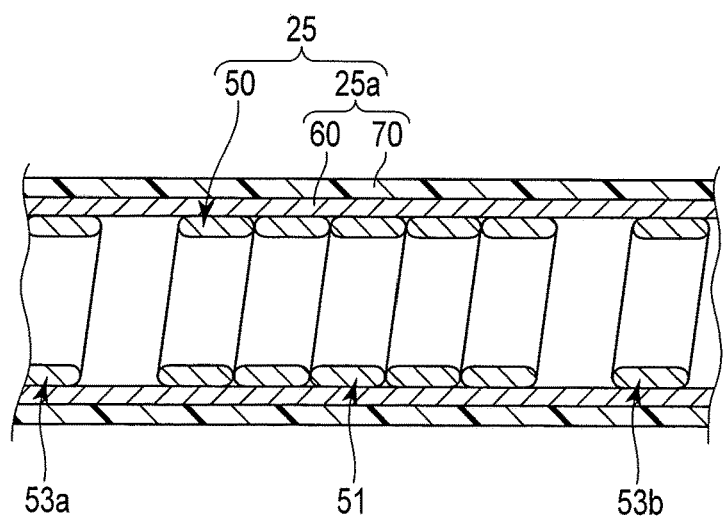
FIG. 3A is a longitudinal sectional view of the three-layered structure of the flexible tube and illustrates a state where a thin plate member of a spiral tube has an oval cross section.

The thin plate member 50a may have various cross sections, including the rectangular cross section shown in FIG. 2A, the oval cross section shown in FIG. 3A, the substantially circular cross section shown in FIG. 3B, and the elliptical cross section shown in FIG. 3C. In the description below, reference will be made to the case where the cross section of the thin plate member 50a of the present embodiment has the rectangular shape shown in FIG. 2A.

[Reticular Tube 60]

The reticular tube 60 is formed by weaving a substantial cylinder using wire bundles. Each bundle is a bundle of stainless steel wires, for example. In the reticular tube 60, the wire bundles intersect with one another and form a lattice-like structure.

[Envelope Portion 70]

The envelope portion 70 is a substantially cylindrical member formed of a flexible resin material, such as a rubber material. The envelope portion 70 has flexibility. The envelope portion 70 may include a thermoplastic elastomer, such as polyurethane or polyester, and a coat layer provided on an outer side of the thermoplastic elastomer.

[Detailed Structure of Spiral Tube 50]

As shown in FIG. 2A, the spiral tube 50 includes a first area portion 50b and a second area portion 50c. The second area portion 50c is a portion different from the first area portion 50b, and is continuous with the first area portion 50b in the direction of the central axis C. In the direction of the central axis C of the spiral tube 50, the first area portion 50*b* is arranged, for example, on a distal end portion of the spiral tube 50, and the second area portion 50*c* is arranged, for example, on a proximal end portion of the spiral tube 50. In the direction of the central axis C, the first area portion 50*b* is located in front of the second area portion 50*c*. A proximal end portion of the first area portion 50*b* is in contact with a distal end portion of the second area portion 50*c*. The thin plate member 50*a* located in the first area portion 50*b* is integral with the thin plate member 50*a* located in the second area portion 50*c*, and is continuous and in contact therewith. Therefore, the first area portion 50*b* is coaxial with the second area portion 50*c*.

[First Area Portion 50*b*]

As shown in FIG. 2A, the first area portion 50*b* includes a densely wound portion 51 which is under an initial tension acting in the direction of the central axis C, and a loosely wound portion 53*a* continuous with at least one end of the densely wound portion 51. In the first area portion 50*b*, the densely wound portion 51 and the loosely wound portion 53*a* are alternately arranged along the central axis C, For example, such that the densely wound portion 51 is arranged at the proximal end of the first area portion 50*b*, and the loosely wound portion 53*a* is arranged at a distal end of the first area portion 50*b*, i.e., at the distal end of the spiral tube 50. As can be seen from the above, the first area portion 50*b* includes, alternately from the distal end thereof to the proximal end thereof, the loosely wound portion 53*a*, the densely wound portion 51, the loosely wound portion 53*a* and the densely wound portion 51. The loosely wound portion 53*a* may be arranged at the proximal end of the first area portion 50*b*. The number of densely wound portions 51 and the number of loosely wound portions 53*a* are not limited to any particular values. The length of each densely wound portion 51 and the length of each loosely wound portion 53*a* are not limited to any particular values.

The loosely wound portion 53*a* arranged at the distal end of the spiral tube 50 is connected to a mouthpiece portion 23*a* at a proximal end of the bendable portion 23 by way of the reticular tube 60. The loosely wound portions 53*a* are provided for the purpose of canceling extension of the spiral tube 50.

Each loosely wound portion 53*a* has a distal end portion and a proximal end portion. The distal end portion is integrally continuous with the densely wound portion 51 located at the distal end side thereof, while the proximal end portion is integrally continuous with the densely wound portion 51 located at the proximal end side thereof. In the direction of the central axis C of the spiral tube 50, the loosely wound portion 53*a* is sandwiched between the densely wound portions 51, and is adjacent to them at the distal end portion and at the proximal end portion. The loosely wound portion 53*a* positioned at the distal end side of the first area portion 50*b* is located adjacent to the densely wound portion 51 only at the proximal end portion.

As shown in FIG. 2A, the first area portion 50*b*, including the densely wound portions 51 and the loosely wound portions 53*a*, is formed by spirally winding the thin plate member 50*a*. The densely wound portions 51 and the loosely wound portions 53*a* are integrally formed using one thin plate member 50*a*. An outer diameter of the densely wound portion 51 and an outer diameter of the loosely wound portion 53*a* are substantially equal to each other.

As shown in FIG. 2A, each densely wound portion 51 is formed like a densely wound coil spring, and the turns of the thin plate member 50*a* which are adjacent in the direction of the central axis C of the spiral tube 50 are in close contact with each other under an initial tension. In other words, no space is provided between the turns of the thin plate member 50*a* which are made adjacent under the initial tension. That is, in the densely wound portion 51, the turns of the thin plate member 50*a* are in close contact with each other in the direction of the central axis C of the spiral tube 50. In the densely wound portion 51, the turns of the thin plate member 50*a* which are adjacent in the direction of the central axis C of the spiral tube 50 are under the initial tension.

As shown in FIG. 2A, each loosely wound portion 53*a* is formed like a loosely wound coil spring, and the turns of the thin plate member 50*a* which are adjacent in the direction of the central axis C of the spiral tube 50 are away from each other, and a space is provided between the adjacent turns. That is, in the loosely wound portion 53*a*, the turns of the thin plate member 50*a* are not in close contact with each other in the direction of the central axis C of the spiral tube 50.

Even though the adjacent turns of the thin plate member 50*a* are not under an initial tension and are not in close contact with each other, the loosely wound portion 53*a* has elasticity. Therefore, both the densely wound portion 51 and the loosely wound portion 53*a* have elasticity. Accordingly, the spiral tube 50 has elasticity.

Since the densely wound portions 51 are under an initial tension, the elasticity of the densely wound portions 51 is increased by the initial tension, and the densely wound portions 51 have higher elasticity than that of the loosely wound portions 53*a*. That is, because of the initial tension, the bouncing property of the densely wound portions 51 is more than that of the loosely wound portions. In other words, the loosely wound portions 53*a* are not under an initial tension, and the elasticity of the loosely wound portions 53*a* is less than that of the densely wound portions 51. Accordingly, the bouncing property of the loosely wound portions 53*a* is less than that of the densely wound portions 51.

[Second Area Portion 50*c*]

As shown in FIG. 2A, the second area portion 50*c* includes only a loosely wound portion 53*b*. Therefore, the proximal end portion of the spiral tube 50 is the loosely wound portion 53*b*. Since the structure of this loosely wound portion 53*b* is similar to that of the loosely wound portion 53*a* of the first area portion 50*b*, a detailed description of the loosely wound portion 53*b* will be omitted. For example, the elasticity of loosely wound portions 53*b* is substantially equal to that of loosely wound portions 53*a*.

As shown in FIG. 2A, a distal end of the loosely wound portion 53*b* is integrally continuous with the proximal end of the densely wound portion 51 arranged at the proximal end of the first area portion 50*b*. That is, the thin plate member 50*a* located in the loosely wound portion 53*b* is continuous with the thin plate member 50*a* located in the densely wound portion 51 of the first area portion 50*b*. An outer diameter of the loosely wound portion 53*b* and the outer diameter of the densely wound portion 51 are substantially equal to each other.

The elasticity of the loosely wound portion 53*b* is set, for example, at a constant value. Therefore, the elasticity of the second area portion 50*c* is constant from the distal end of the second area portion 50*c* to a proximal end thereof.

[Features of Positional Relationship Between First Area Portion 50*b* and Second Area Portion 50*c*]

The second area portion 50*c* does not have an area which is under an initial tension. Since the first area portion 50*b* includes both a densely wound portion 51 and a loosely wound portion 53a, and the second area portion 50c includes only a loosely wound portion 53b, the elasticity of the second area portion 50c is lower than that of the first area portion 50b. In other words, the bouncing property of the first area portion 50b is more than that of the second area portion 50c.

An intestine, such as the large intestine, is a long organ having a number of flexures. In general, in order for an insertion portion of an endoscope to be inserted into the intestine, the flexible tube has to be bent in accordance with the flexures of the intestine and has to return to the straight state by elasticity. However, if the flexible tube is pushed and inserted into the intestine in the bent state conforming to a flexure of the intestine, the flexible tube bent at the time of insertion may push the intestine outward. If this operation has to be repeated, it takes time to insert the insertion portion up to a deep position of the large intestine by way of the flexures of the large intestine.

As a procedure for inserting the flexible tube into the large intestine, the following is known. That is, when the flexible tube passes through a flexure of the intestine, the flexible tube makes that flexure substantially straight by utilization of the elasticity of the flexible tube, and after passing through the substantially straightened flexure, the flexible tube is inserted into the large intestine. Therefore, in order to facilitate the insertion of the flexible tube 25 into the large intestine, the flexible tube 25 should have such high elasticity as enables the intestine to become substantially straight. In this case, the distal end portion of the flexible tube 25, which is inserted first, has to be more elastic than the proximal end portion of the flexible tube 25, which is inserted later.

As shown in FIG. 2A, the flexible tube 25 of the present embodiment is featured in that the first area portion 50b having both a densely wound portion 51 and a loosely wound portion 53a is arranged in the distal end portion of the spiral tube 50, and in that the second area portion 50c having a loosely wound portion 53b is arranged in the proximal end portion of the spiral tube 50. With this structure, the distal end portion of the flexible tube 25 has higher elasticity than the proximal end portion of the flexible tube 25. As a result, the flexible tube 25 has such high elasticity as enables the intestine to become substantially straight.

Since the distal end portion of the flexible tube 25 has such high elasticity, the flexible tube 25 is improved in handling property and insertion-removal property. More specifically, the flexible tube 25 can be easily handled when the intestine is shortened, and can smoothly pass through the descending portion of the transverse colon. Since the distal end portion of the flexible tube 25 has high elasticity, the flexible tube 25 can maintain a straight state even if it is applied with an external force from the intestine, and in this condition the flexible tube 25 can be inserted or removed from the intestine. When the proximal end portion of the flexible tube 25 is twisted, the twisting force is reliably transmitted to the distal end of the flexible tube 25 from the proximal end portion of the flexible tube 25. As a result, the distal end portion of the flexible tube 25 is twisted in accordance with the twisting motion applied to the proximal end portion of the flexible tube 25.

[Initial Tension]

A description will be given of an initial tension of the densely wound portion 51 of the present embodiment.

As shown in FIG. 4A, the initial tension is a force acting in the direction of the central axis C of the densely wound portion 51 such that the edges of the thin plate member 50a of the densely wound portion 51 are brought into close contact with each other. In the densely wound portion 51 in which the adjacent turns of the thin plate member 50a are in close contact with each other in a longitudinal axial direction of the densely wound portion 51, the thin plate member 50a is under an initial tension, and this initial tension is a force which keeps the adjacent turns of the thin plate member 50a in close contact in the longitudinal axial direction against a load smaller than or equal to a predetermined value applied in a radial direction of the flexible tube 25. In other words, when the central axis C of the densely wound portion 51 is horizontal, the preloaded initial tension permits the edges of the thin plate member 50a of the densely wound portion 51 to be in close contact with each other. As a result, the initial tension permits the densely wound portion 51 to be hard to bend and maintain a substantially straight state against an external force (e.g., a force of gravity). When the central axis C of the densely wound portion 51 is vertical, the preloaded initial tension permits the edges of the thin plate member 50a of the densely wound portion 51 to be in close contact with each other against the force of gravity, and maintains a state where no space is provided between the adjacent turns of the thin plate member 50a. The external force F is a force applied to the densely wound portion 51 at an angle to the central axis C of the densely wound portion 51.

The initial tension is defined as a force that permits the edges of the thin plate member 50a to be in close contact with each other, and the entire densely wound portion 51 is under such an initial tension. In this case, the force (initial tension) that permits the edges of the adjacent turns of the thin plate member 50a to be in close contact with each other in the direction of the central axis C can be defined as a close contact force.

By way of example, let us assume that the central axis C of the densely wound portion 51 is horizontal and external force F is applied to the central axis C. In this case, until the external force F exceeds the close contact force (the initial tension) and releases the densely wound portion 51 from the close contact force, no space is generated between the adjacent turns of the thin plate member 50a, and the densely wound portion 51 is not bent. After the external force F applied to the central axis C exceeds the close contact force (the initial tension) and the densely wound portion 51 is released from the close contact force, a space is generated between the adjacent turns of the thin plate member 50a, and the densely wound portion 51 is bent.

Before the densely wound portion 51 begins to bend, the flexural rigidity of the spiral tube 50 increases because of the close contact force of the densely wound portion 51. When the close contact force is canceled by the external force F, and the densely wound portion 51 begins to bend, the spiral tube 50 bends in accordance with the spring constant of the spiral tube 50.

The initial tension mentioned above is imparted to the densely wound portion 51 when the spiral tube 50 is formed, i.e., when the densely wound portion 51 is made. The initial tension to be imparted can be properly adjusted, for example, by a method in which the thin plate member 50a is wound.

The distal end of the spiral tube 50 is fixed to the proximal end of the bendable portion 23, and the proximal end of the spiral tube 50 is fixed to the operation portion 30. The length of the central axis C of the envelope portion 70, as determined in the direction of the central axis C, is substantially unchanged and remains substantially equal, regardless of whether the envelop portion 70 is straight or bends. Thus, the length of the central axis C of the spiral tube 50 covered with the envelope portion 70 is substantially unchanged and remains substantially equal, regardless of whether the spiral tube 50 is straight or bends. Even if, as shown in FIG. 4B, the spiral tube 50 is applied with an external force F in a direction shifted from the central axis C of the flexible tube 25, the length of the central axis C of the spiral tube 50 remains substantially unchanged.

Figure 5A:
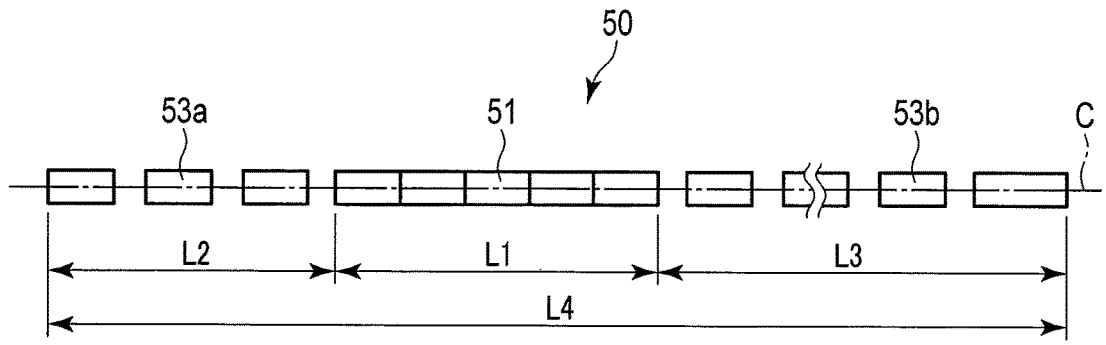
FIG. 5A is a schematic diagram illustrating how the relationships among a length of a central axis of the spiral tube, a length of a central axis of a loosely wound portion, and a length of a central axis of the densely wound portion are in the straight state of the spiral tube.

Let us assume that in the direction of the central axis C of the straight-state spiral tube 50, the length of the central axis C of the densely wound portion 51 is denoted by L1, the length of the central axis C of the loosely wound portion 53a is denoted by L2, the length of the central axis of the loosely would portion 53b is denoted by L3, and the length of the central axis C of the spiral tube 50 is denoted by L4, as shown in FIG. 5A. In this case, the following formula (1) is satisfied:

$$L4=L1+L2+L3 \qquad (1)$$

Figure 5B:
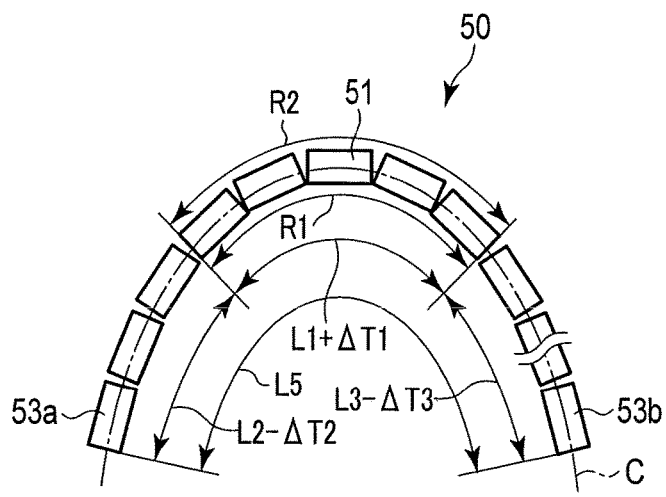
FIG. 5B is a schematic diagram illustrating how the relationships among the length of the central axis of the spiral tube, the length of the central axis of the loosely wound portion, and the length of the central axis of the densely wound portion are in a bent state of the spiral tube.

Let us assume that external force F is applied to the spiral tube 50 in the state depicted in FIG. 5A in a direction shifted from the central axis C of the spiral tube 50, and that the spiral tube 50 is bent in the manner shown in FIG. 5B. The external force F is a force applied to the spiral tube 50 at an angle to the central axis C of the spiral tube 50. As shown in FIG. 5B, in the arc portion R1 on the inner side of the central axis C of the densely wound portion 51, the adjacent turns of the thin plate member 50a are in contact with each other under the initial tension. In the arc portion R2 on the outer side of the central axis C of the densely wound portion 51, the adjacent turns of the thin plate member 50a are separate from each other. Therefore, the length of the central axis C of the densely wound portion 51 in the bent state is more than the length L1 of the central axis C of the densely wound portion 51 in the straight state by ΔT1. That is, the length of the central axis C of the bent densely wound portion 51 is L1+ΔT1.

The length of the central axis C of the densely wound portion 51 is ΔT1 greater in the bent densely wound portion 51 (FIG. 5B) than in the straight densely wound portion 51 (FIG. 5A). In the present embodiment, the loosely wound portions 53a and 53b are arranged such that the densely wound portion 51 is sandwiched between them.

As shown in FIGS. 5A and 5B, when the densely wound portion 51 is bent, the edges of the thin plate member 50a in the loosely wound portion 53a on the distal end side are closer to each other than they are in the straight state. That is, when the densely wound portion 51 is bent, the spaces between the edges of the thin plate member 50a narrow in the loosely wound portion 53a on the distal end side. Therefore, the length of the central axis C of the loosely wound portion 53a on the distal end side is less than the length L2 of the central axis C of the loosely wound portion 53a in the straight state by ΔT2. That is, when the densely wound portion 51 is bent, the length of the central axis C of the loosely wound portion 53a on the distal end side is L2−ΔT2.

As shown in FIGS. 5A and 5B, when the densely wound portion 51 is bent, the edges of the thin plate member 50a in the loosely wound portion 53b on the proximal end side are closer to each other than they are in the straight state. That is, when the densely wound portion 51 is bent, the spaces between the edges of the thin plate member 50a narrow in the loosely wound portion 53b on the proximal end side. Therefore, the length of the central axis C of the loosely wound portion 53b on the proximal end side is less than the length L3 of the central axis C of the loosely wound portion 53b in the straight state by ΔT3. That is, when the densely wound portion 51 is bent, the length of the central axis C of the loosely wound portion 53b on the proximal end side is L3−ΔT3.

Given that the length of the central axis C of the bent spiral tube 50 (FIG. 5B) is L5, the following formula (2) is satisfied:

$$L5=L1+\Delta T1+L2-\Delta T2+L3-\Delta T3 \qquad (2)$$

As described above, the length of the central axis C of the spiral tube 50 has to be substantially unchanged and remain substantially equal, regardless of whether the spiral tube 50 is straight or bent. That is, the following formula (3) has to be satisfied:

$$L4=L5 \qquad (3)$$

By substituting formulas (1) and (2) in formula (3), the following is obtained:

$$L1+L2+L3=L1+\Delta T1+L2-\Delta T2+L3-\Delta T3$$

Hence, the following formula (4) is satisfied:

$$\Delta T1=\Delta T2+\Delta T3 \qquad (4)$$

Formula (4) can be paraphrased as:

(extension of densely wound portion 51)=(contraction of one loosely wound portion 53a)+(contraction of the other loosely wound portion 53b)

As can be seen from this, the extension of the densely wound portion 51 is equal to the sum of the contractions of the loosely wound portions 53a and 53b, and the loosely wound portions 53a and 53b contract in the same amount as the extension of the densely wound portion 51. When the flexible tube 25 is bent, the loosely wound portions 53a and 53b absorb second extension of the spiral tube 50 in the direction of the central axis C of the spiral tube 50, the second extension being caused by first extension of the densely wound portion 51 when the densely wound portion 51 extends in the direction of the central axis C of the spiral tube 50. Accordingly, the loosely wound portions 53a and 53b cancel the second extension. Because the loosely wound portions 53a and 53b are provided, the flexible tube 25 can be smoothly bent, with the characteristics of the densely wound portion 51 maintained (that is, the densely wound portion 51 has higher spring characteristics than those of the loosely wound portions 53a and 53b).

When the insertion portion 20 is inserted into the body cavity (lumen), such as the interior of the large intestine, the operator of the endoscope 10 normally grasps the grasping portion 33 of the operation portion 30 with the left hand, and inserts the distal end of the insertion portion 20 while holding the flexible tube 25 with the right hand.

Let us assume that in the state where the portion corresponding to the densely wound portion 51 of the flexible tube 25 is in the straight state, the flexible tube 25 is inserted into the body cavity (lumen) of the large intestine. Let us also assume that an external force F is applied to the densely wound portion 51 in the direction perpendicular to the central axis C. Where the external force F is smaller than the initial tension acting in the direction of the central axis C, the densely wound portion 51 is allowed to maintain the straight state because of the initial tension. Therefore, the operation force which the operator applies to the flexible tube 25 is transmitted from that position of the flexible tube 25 held by the operator to the distal end portion of the flexible tube 25 (namely, to the distal end portion of the spiral tube 50), and the flexible tube 25 can be easily inserted into the body cavity. That is, the portion corresponding to the densely wound portion 51 of the flexible tube 25 maintains the straight state and is inserted into the lumen.

Where the external force F is larger than the initial tension, the flexible tube 25 is bent, but at the same time, it has the property to return to the straight state. As a result, the bending of the flexible tube 25 is minimal. As a result, the flexible tube 25 can easily return to the straight state.

[Built-in Components 80]

As shown in FIGS. 2A and 2B, the built-in components 80 are contained in the insertion portion 20 and the operation portion 30. The built-in components 80 are insertion members of the endoscope 10 and extend from the distal end hard portion 21 to the operation portion 30 through the bendable portion 23 and the flexible tube 25. In the flexible tube 25, the built-in components 80 are contained in the spiral tube 50 and covered with the spiral tube 50, and are inserted through the spiral tube 50. To be specific, in the spiral tube 50, the built-in components 80 are covered with the densely wound portion 51 and the loosely wound portions 53a and 53b, and extend through the densely wound portion 51 and the loosely wound portions 53a and 53b.

The built-in components 80 include, for example, an illumination unit (not shown), an imaging unit (not shown), a gas sending/water sending tube 85 (shown in FIG. 2B) and a channel 87 (shown in FIG. 2B). The built-in components 80 also include, for example, a bending wire 91 (shown in FIG. 2B) for bending the bendable portion 23, and a wire insertion member 93 (shown in FIG. 2B) through which the bending wire 91 is inserted.

As shown in FIG. 2B, the illumination unit includes, for example, an illumination cable 81, and the imaging unit includes, for example, an image cable 83.

A distal end of the bending wire 91 is connected to the distal end hard portion 21, and a proximal end thereof is connected to the bending operation portion 37. When the bending operation portion 37 is operated, the bending wire 91 is pulled, and the bendable portion 23 is bent. As described above, for example, the bending wire 92 serves as an operation member for operating the bendable portion 23 which serves as an actuation portion of the endoscope 10.

As shown in FIG. 2B, a plurality of bending wires 91 (for example, two pairs of bending wires 91) are employed. With this structure, the bendable portion 23 can be bent in four directions, including an upward (U) direction, a downward (D) direction, a leftward (L) direction and a rightward (R) direction. Alternatively, a plurality of wires, including one pair of bending wires 91, may be employed. With this structure, the bendable portion 23 can be bent in two directions, including an upward (U) direction and a downward (D) direction.

As shown in FIG. 2B, the wire insertion member 93 is inserted into the spiral tube 50. For example, a proximal end of the wire insertion member 93 is an end fixed inside the main body portion 31, while a distal end of the wire insertion member 93 is an end fixed inside the distal end portion of the spiral tube 50. As shown in FIG. 2B, the number of wire insertion members 93 is the same as the number of bending wires 91. In the present embodiment, a plurality of wire insertion members 93 are employed, and one bending wire 91 is inserted into each of the wire insertion members 93.

The wire insertion member 93 has desirable elasticity. Such a wire insertion member 93 is formed, for example, by spirally winding a linear member. That is, the wire insertion member 93 is a spiral elastic tube (coil pipe) having elasticity. The linear member of the wire insertion member 93 is, for example, a stainless steel wire. The wire insertion member 93 is formed such that the adjacent turns of the linear member are in close contact with each other, with no space provided between them in the direction of a central axis of the wire insertion member 93. The wire insertion member 93 is formed such that when an external force F is applied to the wire insertion member 93, a space is formed between the adjacent turns of the linear member, and the wire insertion member 93 is allowed to bend. The external force F is a force applied to the wire insertion member 93 at an angle to the central axis of the wire insertion member 93. The wire insertion member 93 is formed, for example, like a densely wound coil spring or a densely wound coil.

The cross section of the linear member has a substantially circular shape, such as that shown in FIG. 2A. Like the spiral tube 50, the linear member may have various cross sections, including an rectangular cross section, the elongated circle cross section shown in FIG. 3A, and the elliptical cross section shown in FIG. 3C. In the description below, reference will be made to the case where the cross section of the linear member 50a of the present embodiment has the substantially circular shape shown in FIG. 2A.

[Supplemental Description of Elasticity of Spiral Tube 50]

In general, the insertion-removal property which the flexible tube has in the body cavity (lumen) of the large intestine is dependent on the flexibility (bending easiness) of the flexible tube and the elasticity of the flexible tube (which represents how easily the bent flexible tube returns to the straight state).

In the present embodiment, in order for the flexible tube 25 to have desirable elasticity, a densely wound portion 51 is employed, which is under an initial tension acting in the direction of the central axis C of the densely wound portion 51. In order to increase the elasticity of the flexible tube 25, the spiral tube 50 has to be under a large initial tension. In general, a larger initial tension can be imparted to the spiral tube by increasing the plate thickness of the spiral thin plate member with which to form the spiral tube. However, an increase in the plate thickness inevitably results in an increase in the diameter of the spiral tube. If the diameter of the spiral tube is large, the insertion-removal property of the flexible tube may be degraded.

As shown in FIGS. 2A and 2B, the spiral tube 50 contains the built-in component 80, and the built-in component 80 can have a supplement area portion 57 which is under initial tensions A and B (not shown) throughout the length thereof and which supplements the elasticity of the spiral tube 50. The built-in component 80 is contained in the spiral tube 50. In the state where the built-in component 80 is inserted in the spiral tube 50, the supplement area portion 57 is provided at such portions which are covered with the spiral tube 50. In other words, in the state where the built-in component 80 is inserted in the spiral tube 50, the supplement area portion 57 overlaps the first area portion 50b and the second area portion 50c. With this structure, the elasticity of the spiral tube 50 is supplemented by the supplement area portion 57 with no need to increase the plate thickness of the thin plate member 50a.

In general, in the procedure for inserting the flexible tube 25 into the large intestine, it is desired that the distal end portion of the flexible tube 25 has higher elasticity than the proximal end portion of the flexible tube 25.

For this reason, as shown in FIG. 2A, the supplement area portion 57 includes the first supplement area portion 57a which is under the large initial tension A, and the second supplement area portion 57b which is under the initial tension B smaller than the initial tension A of the first supplement area portion 57a. To make clear distinction between the first supplement area portion 57a and the second supplement area portion 57b in the drawings, they are indicated in different ways in the drawings. For example, in the built-in component, the first supplement area portion 57a is indicated by black circles, and the second supplemental area portion 57b is indicated by white circles. Initial tension A is uniform, for example, throughout the whole length of the first supplement area portion 57a. Initial tension B is uniform, for example, throughout the whole length of the second supplement area portion 57b. Initial tensions A and B may be equal to the initial tension of the densely wound portion 51. Alternatively, they may be slightly higher or lower than the initial tension of the densely wound portion 51. Initial tensions A and B act in the direction of the central axis C. Since initial tensions A and B are substantially similar to the initial tension of the densely wound portion 51, a detailed description of initial tensions A and B will be omitted.

As shown in FIG. 2A, the first supplement area portion 57a is located on a more distal end portion side of the built-in component 80 than the second supplemental area portion 57b, as viewed in the direction of the central axis C of the spiral tube 50. In other words, the first supplement area portion 57a is located forward of the second supplemental area portion 57b. With this structure, the distal end portion of the built-in component 80 has higher elasticity than the proximal end portion of the built-in component 80.

As shown in FIG. 2A, the first supplement area portion 57a is covered with the entirety of the first area portion 50b, and the second supplement area portion 57b is covered with the proximal end portion side of the second area portion 50c. In other words, the first supplement area portion 57a overlaps the first area portion 50b, and the second supplement area 57b overlaps the second area portion 50c.

With this structure, the distal end portion of the flexible tube 25 is supplemented to have high elasticity, while the proximal end portion of the flexible tube 25 is supplemented to have low elasticity. In other words, the distal end portion of the flexible tube 25 has higher elasticity than the proximal end portion of the flexible tube 25. Therefore, in the procedure for inserting the flexible tube 25 into the large intestine, the flexible tube 25 makes a flexure of the intestine substantially straight, and after passing through the straightened flexure, the flexible tube is inserted into the large intestine.

The supplement of elasticity contributes to the improvement of the handling property and insertion-removal property of the flexible tube 25. More specifically, the flexible tube 25 can be easily handled when the intestine shortens, and can smoothly pass through the descending portion of the transverse colon. Even when the flexible tube 25 is applied with an external force from the intestine, the flexible tube 25 maintains a straight state, and in this condition the flexible tube 25 can be inserted or removed from the intestine. When the proximal end portion of the flexible tube 25 is twisted, the twisting force is reliably transmitted to the distal end portion of the flexible tube 25 from the proximal end portion of the flexible tube 25. As a result, the distal end portion of the flexible tube 25 is twisted in accordance with the twisting motion applied to the proximal end portion of the flexible tube 25.

As shown in FIG. 2A, the spiral tube 50 includes a connection part 55 communicating with both the first area portion 50b and the second area portion 50c. The connection part 55 is defined by a proximal end of the first area portion 50b and a distal end of the second area portion 50c which is communicated the proximal end of the first area portion 50b. The connection part 55 is a portion where the thin plate member 50a changes from the densely wound portion 51 to the loosely wound portion 53b.

In the manufacturing process of the spiral tube 50, the elasticity of the spiral tube 50 differs between the first area portion 50b and the second area portion 50c by the initial tension. Because of the initial tension, the elasticity of the spiral tube 50 is high in the first area portion 50b and low in the second area portion 50c. That is, the elasticity of the spiral tube 50 changes greatly at the connection part 55. In other words, the connection part 55 is a portion where the elasticity of the densely wound portion 51 and the elasticity of the loosely wound portion 53a change and where the elasticity of the spiral tube 50 varies.

Therefore, where an external force F which is less than the initial tension is applied to the spiral tube 50, the entirety of the spiral tube 50 does not bend in such a desirable manner as to form an arc.

For example, the spiral tube 50 is bent at the loosely wound portions 53a and 53b and remains straight at the connection part 55 and the densely wound portion 51. Alternatively, the spiral tube 50 is greatly bent at the loosely wound portions 53a and 53b and is slightly bent at the connection part 55 and the densely wound portion 51 by the initial tension. The spiral tube 50 bends differently between the connection part 55 and the densely wound portion 51.

If the external force by which the spiral tube 50 is bent is not applied to the spiral tube 50, the entirety of the spiral tube 50 does not return to the original straight state. The spiral tube 50 returns to the slightly bent state at the loosely wound portions 53a and 53b and returns to the straight state at the connection part 55 and the densely wound portion 51. That is, the straightness changes at the connection part 55.

As shown in FIG. 2A, the boundary part 57c between the first supplement area portion 57a and the second supplement area portion 57b, as viewed in the direction of the central axis C, has such a structure as prevents the elasticity of the spiral tube 50 from changing greatly at the connection part 55. That is, in the state where the built-in component 80 are inserted in the spiral tube 50, the boundary part 57c described above is covered with a portion other than the connection part 55 between the first area portion 50b and the second area portion 50c, in the direction of the central axis C of the spiral tube 50. More specifically, as shown in FIG. 2A, in the state where the built-in component 80 are inserted in the spiral tube 50, the boundary part 57c is covered with the distal end portion of the second area portion 50c. More specifically, the boundary part 57c is located at a position shifted from the distal end of the loosely wound portion 53b to the proximal end portion thereof by a distance corresponding to 2 to 5 pitches of the loosely wound portion 53b. As described, the boundary part 57c is located on the more proximal end portion side of the loosely wound portion 53b than the connection part 55.

As shown in FIG. 2A, therefore, the first supplement area portion 57a is inserted into the distal end portion of the second area portion 50c and overlaps the second area portion 50c. In the direction of the central axis C of the spiral tube 50, the first supplement area portion 57a is covered with the entirety of the first area portion 50b and is also covered with the distal end portion of the second area portion 50c.

In this manner, the supplement area portion 57 (the first supplement area portion 57a) supplements the elasticity of the spiral tube 50 at the connection part 55. The elasticity of the spiral tube 50 is prevented from varying at the connection part 55, and the rapid change of the elasticity of the spiral tube 50 is suppressed. The connection part 55, which supplements the elasticity of the spiral tube 50, bends in a similar manner to that of the first area portion 50b, and the entirety of the spiral tube 50 bends at such a desirable curvature as to form an arc.

When the flexible tube 25 is bent, the built-in component 80 may be shifted relative to the spiral tube 50 in the direction of the central axis C of the built-in component 80. In such a case, for example, the boundary part 57c and the first supplement area portion 57a (located on the front side of the boundary part 57c) are shifted from the distal end portion of the second area portion 50c to the connection part 55 and are covered with the connection part 55. In this manner, the first supplement area portion 57a supplements the elasticity of the spiral tube 50 at the connection part 55. The elasticity of the spiral tube 50 is prevented from varying at the connection part 55, and the rapid change of the elasticity of the spiral tube 50 is suppressed. The connection part 55, which supplements the elasticity of the spiral tube 50, bends in a similar manner to that of the first area portion 50b, and the entirety of the spiral tube 50 bends at such a desirable curvature as to form an arc. When the application of the external force F which bends the connection part 55 stops, the connection part 55 is made to return to the straight state by the first supplement area portion 57a.

As shown in FIG. 2A, the first supplement area portion 57a is longer than the first area portion 50b, is inserted through the connection part 55, and is inserted into the distal end portion of the second area portion 50c. Therefore, the built-in component 80 having the supplement area portion 57 is longer than the spiral tube 50 and configured in such a manner that the distal end of the first supplement area portion 57a is projected from the distal end of the spiral tube 50 (which is the distal end of the first area portion 50b) toward the bendable portion 23. For example, the distal end of the built-in component 80 having the supplement area portion 57 is a free end, and the proximal end of that built-in component 80 is a fixed end.

[Example of Built-in Component 80 Having Supplement Area Portion 57]

A description will be given of an example of a built-in component 80 having the supplement area portion 57 described above.

As shown in FIGS. 2A and 2B, the built-in component 80 include, for example, at least one built-in densely wound member 95 which is formed by spirally winding a linear member 95a in the form of a coil and which has a supplement area portion 57. In the present embodiment, one built-in densely wound member 95 is employed. Since the built-in densely wound member 95 in the form of a coil has a supplement area portion 57, the built-in densely wound member 95 is under initial tensions A and B acting in the direction of the central axis of the built-in densely wound member 95. The supplement area portion 57 to which initial tensions A and B are imparted is provided for the built-in densely wound member 95. The built-in densely wound member 95 functions like the densely wound portion 51 described above. That is, the built-in densely wound member 95 functions as a spiral elastic member having a predetermined elasticity. The built-in densely wound member 95 is formed like a coil pipe (a densely wound coil spring). The linear member 95a is, for example, a stainless steel wire.

The cross section of the linear member 95a has a substantially circular shape, such as that shown in FIG. 2A. Like the spiral tube 50, the linear member 95a may have various cross sections, including an rectangular cross section, the elongated circle cross section shown in FIG. 3A, and the elliptical cross section shown in FIG. 3C. In the description below, reference will be made to the case where the cross section of the linear member 50a of the present embodiment has the substantially circular shape shown in FIG. 2A.

As shown in FIG. 2B, the built-in densely wound member 95 is a member provided independently of the wire insertion member 93. In the direction around the central axis C of the spiral tube 50 (FIG. 2B), the built-in densely wound member 95 is located adjacent to one wire insertion member 93.

A description will now be given of the structure of the built-in densely wound member 95 for which the supplement area portion 57 is arranged.

As shown in FIG. 2A, the built-in densely wound member 95 includes the first supplement area portion 57a and the second supplement area portion 57b.

The first supplement area portion 57a of the built-in densely wound member 95 is formed as a densely wound member in which the large initial tension A acts, and the second supplement area portion 57b thereof is formed as a loosely wound member in which the small initial tension B acts. To make clear distinction between the first supplement area portion 57a and the second supplement area portion 57b in the drawings, they are indicated in different ways in the drawings. For example, in the built-in densely wound member 95, the first supplement area portion 57a is indicated by black circles, and the second supplemental area portion 57b is indicated by white circles.

The built-in densely wound member 95 in the first supplement area portion 57a and the built-in densely wound member 95 in the second supplement area portion 57b have substantially a similar structure to that of the densely wound portion 51. That is, the built-in densely wound member 95 is formed such that the adjacent turns of the linear member 95a, as viewed in the direction of the central axis of the built-in densely wound member 95, are in close contact with each other under initial tensions A and B, with no space provided between the adjacent turns by initial tensions A and B.

As shown in FIG. 2A, the built-in densely wound member 95 in the first supplement area portion 57a and the built-in densely wound member 95 in the second supplement area portion 57b are integrally formed of the same linear member 95a. A proximal end of the built-in densely wound member 95 in the first supplement area portion 57a is connected to a distal end of the built-in densely wound member 95 in the second supplement area portion 57b. As described, the built-in densely wound member 95 in the first supplement area portion 57a and the built-in densely wound member 95 in the second supplement area portion 57b are integral with each other.

Let us assume that an external force F that is less than initial tensions A and B is applied to the first supplement area portion 57a and the second supplement area portion 57b. In this case, no space is created between the adjacent turns of the linear member 95a, and neither the first supplement area portion 57a nor the second supplement area portion 57b bends.

Let us assume that an external force F that is more than initial tension B and less than initial tension A is applied to the first supplement area portion 57a and the second supplement area portion 57b. In this case, the first supplement area portion 57a does not bend, while the second supplement area portion 57b bends, with a space being created between the adjacent turns of the linear member 95a in the second supplement area portion 57b.

Let us assume that an external force F that is more than initial tension A is applied to the first supplement area portion 57a and the second supplement area portion 57b. In this case, a space is created between the adjacent turns of the linear member 95a, and both the first supplement area portion 57a and the second supplement area portion 57b bend.

The built-in densely wound member 95 has elasticity. Therefore, both the first supplement area portion 57a and the second supplement area portion 57b have elasticity. However, the elasticity of the first supplement area portion 57a is high because the first supplement area portion 57a is under initial tension A. On the other hand, the elasticity of the second supplement area portion 57b is low because the second supplement area portion 57b is under initial tension B. As can be seen from this, the elasticity of the first supplement area portion 57a is higher than that of the second supplement area portion 57b. Being under initial tension A, the first supplement area portion 57a is harder to bend than the second supplement area portion 57b. In other words, the elasticity of the second supplement area portion 57b is lower than that of the first supplement area portion 57a. The second supplement area portion 57b is more flexible and easier to bend than the first supplement area portion 57a.

[Relative Position Relationship Between Spiral Tube 50 and Built-in Densely Wound Member 95 for which First Supplement Area Portion 57a and Second Supplement Area Portion 57b are Provided]

As shown in FIG. 2A, the loosely wound portion 53a and the densely wound portion 51 are alternately arranged in the spiral tube 50 from the distal end thereof to the proximal end thereof such that the loosely wound portion 53a is foremost and the densely would portion 51 is rearmost. A loosely wound portion 53b is arranged at a proximal end of the rearmost densely wound portion 51.

As shown in FIG. 2A, the first supplement area portion 57a and the second supplement area portion 57b are arranged in the built-in densely wound member 95 from the distal end thereof to the proximal end thereof.

As shown in FIG. 2A, in the state where the built-in densely wound member 95 is inserted in the spiral tube 50, the first supplement area portion 57a is covered with the entirety of the first area portion 50b and the distal end portion of the second area portion 50c, while the second supplement area portion 57b is covered with the proximal end portion of the second area portion 50c. In this state, the first supplemental area portion 57a is covered with the densely wound portion 51 and the loosely wound portions 53a and 53b, while the second supplemental area portion 57b is covered only with the loosely wound portion 53b.

As shown in FIG. 2A, the first supplement area portion 57a is longer than the first area portion 50b, is inserted through the connection part 55, and is inserted and received in the distal end portion of the second area portion 50c. The first supplement area portion 57a is arranged in the first area portion 50b and also in the distal end portion of the second area portion 50c.

The second supplement area portion 57b is inserted and received in the second area portion 50c.

[Operation]

In the present embodiment, the spiral tube 50 includes a densely wound portion 51 under an initial tension, and loosely wound portions 53a and 53b. The flexible tube 25 includes this spiral tube 50 as well as the built-in component 80 having a supplement area portion 57.

When the flexible tube 25 is inserted or removed from the body cavity (lumen) of the large intestine, an external force F is applied to the flexible tube 25 from the body wall.

[Operation 1]

Where the external force F is smaller than the initial tension, the densely wound portion 51 maintains the straight state because of the initial tension. In other words, when the external force F smaller than the initial tension is exerted on the densely wound portion 51, the initial tension keeps the densely wound portion 51 in the state where no space is created between the adjacent turns of the thin plate member 50a, and the adjacent turns of the thin plate member 50a remain in close contact with each other.

At the same time, the loosely wound portions 53a and 53b are about to be bent by the external force F. In the present embodiment, the spiral tube 50 contains the built-in densely wound member 95 including the supplement area portion 57 to which initial tensions A and B are imparted. More specifically, the first supplement area portion 57a overlaps and is covered with the first area portion 50b and the distal end portion of the second area portion 50c. The second supplement area portion 57b overlaps and is covered with the proximal end portion of the second area portion 50c. With this structure, the elasticity of the loosely wound portions 53a and 53b is supplemented by the first supplement area portion 57a to which initial tension A is imparted and by the second supplement area portion 57b to which initial tension B is imparted. Accordingly, the elasticity of the loosely wound portions 53a and 53b is increased by the first supplement area portion 57a and the second supplement area portion 57b, such that the increased elasticity is as high as the elasticity of the densely wound portion 51. As long as the external force F is less than initial tensions A and B, the loosely wound portions 53a and 53b whose elasticity is supplemented maintain the straight state like the densely wound portion 51, because of the first supplement area portion 57a to which initial tension A is imparted and the second supplement area portion 57b to which initial tension B is imparted.

As can be seen from this, the flexible tube 25 provides elasticity based on the initial tension at any portion throughout the length thereof, and that elasticity is provided by the densely wound portion 51, the first supplement area portion 57a and the second supplement area portion 57b. As a result, the flexible tube 25 can maintain the straight state because of the densely wound portion 51, the first supplement area portion 57a and the second supplement area portion 57b. Even if the flexible tube 25 is bent, it can easily return to the straight state. Owing to this, the amount of bending can be easily made zero (straight state), and the flexible tube 25 can be easily made straight. The force which the operator applies for insertion or removal of the flexible tube 25 can be easily transmitted to the flexible tube 25, and the flexible tube 25 can be easily inserted into the body cavity or removed therefrom.

More specifically, the insertion-removal property of the flexible tube 25 which the flexible tube 25 has in the body cavity (lumen) of the large intestine is dependent on the flexibility (bending easiness) of the flexible tube 25 and the elasticity of the flexible tube 25 (which represents how easily the bent flexible tube returns to the straight state).

In the present embodiment, in order for the flexible tube 25 to have desirable elasticity, the densely wound portion 51 is employed, which is under an initial tension. In order to increase the elasticity of the flexible tube 25, the spiral tube 50 has to be under a large initial tension. In general, a larger initial tension is imparted to the spiral tube by increasing the plate thickness of the spiral thin plate member with which to form the spiral tube. An increase in the plate thickness inevitably results in an increase in the diameter of the spiral tube. If the diameter of the spiral tube is large, the insertion-removal property of the flexible tube may be degraded.

However, in the present embodiment, the elasticity of the flexible tube 25 is not solely dependent on the initial tension of the densely wound portion 51 but is supplemented by the first supplement area portion 57a and the second supplement area portion 57b. Since the first supplement area portion 57a and the second supplement area portion 57b are provided, it is not necessary to increase the plate thickness of the spiral thin plate member 50a with which to form the spiral tube 50.

In the flexible tube 25, the first supplement area portion 57a and the second supplement area portion 57b ensure desirable elasticity and insertion-removal property. As long as the external force F is less than the initial tension, the flexible tube 25 is inserted into the body cavity while maintaining the straight state. Therefore, the insertion-removal property of the flexible tube 25 can be enhanced.

[Operation 2]

Where the external force F is not less than the initial tension, the densely wound portion 51 bends even though it is under an initial tension and has high elasticity.

In the present embodiment, the first area portion 50b having both a densely wound portion 51 and a loosely wound portion 53a is arranged in the distal end portion of the spiral tube 50, and the second area portion 50c having a loosely wound portion 53b is arranged in the proximal end portion of the spiral tube 50.

With this structure, the distal end portion of the flexible tube 25 has higher elasticity than the proximal end portion of the flexible tube 25. Therefore, in the procedure for inserting the flexible tube 25 into the large intestine, the flexible tube 25 makes a flexure of the intestine substantially straight, and after passing through the straightened flexure, the flexible tube 25 is inserted into the large intestine.

The first supplement area portion 57a is located on the more distal end portion side of the built-in components 80 than the second supplemental area portion 57b, as viewed in the direction of the central axis C of the spiral tube 50. With this structure, the distal end portion of the built-in component 80 has higher elasticity than the proximal end portion of the built-in component 80.

The first supplement area portion 57a is covered with the entirety of the first area portion 50b, and the second supplement area portion 57b is covered with the proximal end portion of the second area portion 50c. With this structure, the distal end portion of the flexible tube 25 is supplemented to have high elasticity, while the proximal end portion of the flexible tube 25 is supplemented to have low elasticity. In other words, the distal end portion of the flexible tube 25 has higher elasticity than the proximal end portion of the flexible tube 25. Therefore, in the procedure for inserting the flexible tube 25 into the large intestine, the flexible tube 25 makes a flexure of the intestine substantially straight, and after passing through the straightened flexure, the flexible tube 25 is inserted into the large intestine.

The supplement of elasticity contributes to the improvement of the handling property and insertion-removal property of the flexible tube 25. More specifically, the flexible tube 25 can be easily handled when the intestine shortens, and can smoothly pass through the descending portion of the transverse colon. Even when the flexible tube 25 is applied with an external force from the intestine, the flexible tube 25 maintains a straight state, and in this condition the flexible tube 25 can be inserted or removed from the intestine. When the proximal end portion of the flexible tube 25 is twisted, the twisting force is reliably transmitted to the distal end portion of the flexible tube 25 from the proximal end portion of the flexible tube 25. As a result, the distal end portion of the flexible tube 25 is twisted in accordance with the twisting motion applied to the proximal end portion of the flexible tube 25.

The boundary part 57c between the first supplement area portion 57a and the second supplement area portion 57b is covered with a portion other than the connection part 55 between the first area portion 50b and the second area portion 50c. To be specific, the boundary part 57c is covered with the second area portion 50c.

With this structure, the supplement area portion 57 (the first supplement area portion 57a) supplements the elasticity of the spiral tube 50 at the connection part 55. The elasticity of the spiral tube 50 is prevented from varying at the connection part 55, and the rapid change of the elasticity of the spiral tube 50 is suppressed. The connection part 55, which supplements the elasticity of the spiral tube 50, bends in a similar manner to that of the first area portion 50b, and the entirety of the spiral tube 50 bends at such a desirable curvature as to form an arc.

The elasticity of the spiral tube 50 is prevented from varying at each part throughout the length, and the rapid change of the elasticity of the spiral tube 50 is suppressed. The entirety of the spiral tube 50 smoothly bends at such a desirable curvature as to form an arc. As a result, the spiral tube 50 can be inserted into the large intestine and can pass along the flexures of the large intestine. As a result, the flexible tube 25 can be easily inserted into the body cavity or removed therefrom. Therefore, the insertion-removal property of the flexible tube 25 can be enhanced.

When the flexible tube 25 comes into contact with a flexure of the large intestine, it is gradually bent by the external force F. Since the large intestine is not strongly pushed or is not applied with a high tension, the patient does not feel much discomfort.

[Operation 3]

In the spiral tube 50, the densely wound portion 57 is under an initial tension and therefore has high elasticity, while the loosely wound portions 53a and 53b have low elasticity. When the entirety of the flexible tube 25 is applied with an external force F from a flexure of the body cavity, the densely wound portion 51 greatly pushes up or bounces the flexure against the external force F, and the loosely wound portions 53a and 53b slightly push up or bounce the flexure against the external force F. That is, the upward force applied by the densely wound portion 51 is larger than that applied by the loosely wound portions 53a and 53b. If the upward force of the spiral tube 50 differs, depending upon the portions, the spiral tube 50 cannot push back a flexure of the large intestine with a uniform force. As a result, the insertion-removal property of the flexible tube 25 is degraded.

In the present embodiment, however, the spiral tube 50 contains the built-in densely wound member 95 including a supplement area portion 57 to which initial tensions A and B are imparted. More specifically, the first supplement area portion 57a of the built-in densely wound member 95 overlaps and is covered with the first area portion 50b and the distal end portion of the second area portion 50c. The second supplement area portion 57b overlaps and is covered with the proximal end portion of the second area portion 50c. With this structure, the low elasticity of the loosely wound portions 53a and 53b is supplemented by the first supplement area portion 57a to which initial tension A is imparted and by the second supplement area portion 57b to which initial tension B is imparted. Accordingly, the elasticity of the loosely wound portions 53a and 53b is increased such that the increased elasticity is as high as the elasticity of the densely wound portion 51. The upward force of the spiral tube 50 is therefore substantially uniform, and the spiral tube 50 can push back a flexure of the large intestine with a uniform force. As a result, the insertion-removal property of the flexible tube 25 is improved.

[Operation 4]

If no external force is applied, the densely wound portion 51 having high elasticity returns to the original straight state. Like the densely wound portion 51, the loosely wound portions 53a and 53b (whose elasticity is supplemented by the first and second supplement area portions 57a and 57b which are under initial tensions A and B, respectively) return to the straight state. In this manner, the entirety of the flexible tube 25 returns to the straight state.

[Operation 5]

The first supplement area portion 57a is longer than the first area portion 50b, is inserted through the connection part 55, and is inserted into the distal end portion of the second area portion 50c.

When the flexible tube 25 is bent in this state, the built-in component 80 may be shifted relative to the spiral tube 50 in the direction of the central axis C of the built-in component 80.

In such a case as well, for example, the first supplement area portion 57a located on the front side of the boundary part 57c is shifted from the distal end portion of the second area portion 50c to the connection part 55 and is covered with the connection part 55. In this manner, the first supplement area portion 57a supplements the elasticity of the spiral tube 50 at the connection part 55. The elasticity of the spiral tube 50 is prevented from varying at the connection part 55, and the rapid change of the elasticity of the spiral tube 50 is suppressed. Accordingly, when the external force F is smaller than the initial tension, the connection part 55 maintains the straight state. As long as the external force F is not less than the initial tension, the connection part 55 smoothly bends at such a desirable curvature as to form an arc. When the application of the external force F which bends the connection part 55 stops, the connection part 55 returns to the straight state.

[Advantages]

As described above, in the present embodiment, the spiral tube 50 includes the supplement area portion 57 to which initial tensions A and B serving to supplement the elasticity of the spiral tube 50 throughout the overall length are imparted. In the present embodiment, therefore, the elasticity of the flexible tube 25 is not solely dependent on the initial tension of the densely wound portion 51 but can be supplemented by the first supplement area portion 57a and the second supplement area portion 57b. Since the first supplement area portion 57a and the second supplement area portion 57b are provided in the present embodiment, it is not necessary to increase the plate thickness of the spiral thin plate member 50a with which to form the spiral tube 50.

The present embodiment can therefore provide a flexible tube 25 in which the first and second supplement area portions 57a and 57b under respective initial tensions ensure desirable elasticity and insertion-removal property. Since the flexible tube 25 of the present embodiment easily maintains the straight state and can be easily inserted into the body cavity, the insertion-removal property of the flexible tube 25 can be enhanced. In the present embodiment, the distal end portion of the flexible tube 25 can be reliably twisted in accordance with the twisting motion applied to the proximal end portion of the flexible tube 25. When the proximal end portion of the flexible tube 25 grasped by the operator is twisted, the twisting force is reliably transmitted to the distal end of the flexible tube 25, and the distal end portion of the flexible tube 25 can be reliably twisted in response to the twisting motion applied to the proximal end portion of the flexible tube 25.

In the present embodiment, the plate thickness of the spiral tube 50 and the plate thickness of the envelope portion 70 need not be increased, and the outer diameter of the flexible tube 25 does not increase. Thus, the flexible tube 25 can be made as thin as possible. The use of such a thin flexible tube minimizes the pain of the patient. According to the present embodiment, the internal space of the spiral tube 50 is not narrow, the built-in components 80 inside the flexible tube 25 are not pressed tightly, and the flexibility of the flexible tube 25 is not degraded.

In the present embodiment, the boundary part 57c between the first supplement area portion 57a and the second supplement area portion 57b is covered with a portion other than the connection part 55 between the first area portion 50b and the second area portion 50c. To be specific, the boundary part 57c is covered with the second area portion 50c. In the present embodiment, therefore, the elasticity of the spiral tube 50 is prevented from varying at each part throughout the length, and the rapid change of the elasticity of the spiral tube 50 can be suppressed. In the present embodiment, the entirety of the spiral tube 50 can be smoothly bent at such a desirable curvature as to form an arc. According to the present embodiment, the spiral tube 50 can be inserted into the large intestine and pass along the flexures of the large intestine. As a result, the flexible tube 25 can be easily inserted into the body cavity or removed therefrom. According to the present embodiment, the insertion-removal property of the flexible tube 25 can be enhanced.

Since the flexible tube 25 of the present embodiment bends in response to an external force F, it does not strongly push the large intestine even when it is in contact with a flexure of the large intestine. According to the present embodiment, the tension applied to the large intestine is not high, and the patient does not feel much discomfort.

In the present embodiment, the first area portion 50b having both a densely wound portion 51 and a loosely wound portion 53a is arranged in the distal end portion of the spiral tube 50, and the second area portion 50c having a loosely wound portion 53b is arranged in the proximal end portion of the spiral tube 50. Thus, the distal end portion of the flexible tube 25 has higher elasticity than the proximal end portion of the flexible tube 25. In the procedure for inserting the flexible tube 25 into the large intestine, the flexible tube 25 can make a flexure of the intestine substantially straight, and after passing through the straightened flexure, the flexible tube 25 can be inserted into the large intestine. According to the present embodiment, the insertion-removal property of the flexible tube 25 can be enhanced.

In the present embodiment, the first supplement area portion 57a is located on the more distal end portion side of the spiral tube 50 than the second supplemental area portion 57b, as viewed in the direction of the central axis C of the spiral tube 50. The first supplement area portion 57a is covered with the entirety of the first area portion 50b and the distal end portion of the second area portion 50c, and the second supplement area portion 57b is covered with the proximal end portion of the second area portion 50c.

According to the present embodiment, in the procedure for inserting the flexible tube 25 into the large intestine, the flexible tube 25 can make a flexure of the intestine substantially straight, and after passing through the straightened flexure, the flexible tube 25 can be inserted into the large intestine. According to the present embodiment, the insertion-removal property of the flexible tube 25 can be enhanced.

According to the present embodiment, the upward force of the spiral tube 50 can be supplemented by the supplement area portion 57, and the spiral tube 50 can push back a flexure of the large intestine with a uniform force. As a result, the insertion-removal property of the flexible tube 25 can be enhanced.

According to the present embodiment, when the external force F that cancels the close contact force based on the initial tension is not applied to the flexible tube 25, the entirety of the flexible tube 25 can be returned to the straight state by the elasticity based on the initial tension of the supplement area portion 57.

In the present embodiment, the built-in densely wound member 95 is a member provided independently of the wire insertion member 93. In the present embodiment, therefore, the built-in densely wound member 95 does not have to have another function and can be designed only to supplement elasticity.

The initial tension of the supplement area portion 57 may be uniform along the overall length of the supplement area portion 57. In other words, the supplement area portion 57 may include only one of the first supplement area portion 57a and the second supplement area portion 57b.

The supplement area portion 57 may be provided along the overall length of the built-in component 80. In other words, the supplement area portion 57 may be provided not only at those portions of the built-in component 80 which are covered with the spiral tube 50 but also at those portions of the built-in component 80 which are covered with the operation portion 30.

The supplement area portion 57 may be under a high initial tension at portions covered with the spiral tube 50, and may be under a low initial tension at portions covered with the operation portion 30. The supplement area portion 57 may be under no initial tension at portions covered with the operation portion 30.

The boundary part 57c may be covered with the proximal end portion of the first area portion 50b. In the present embodiment, the entirety of the spiral tube 50 can be smoothly bent at such a desirable curvature as to form an arc.

For example, in the boundary part 57c, the initial tension may gradually decrease from the first supplement area portion 57a to the second supplement area portion 57b.

Figure 6:
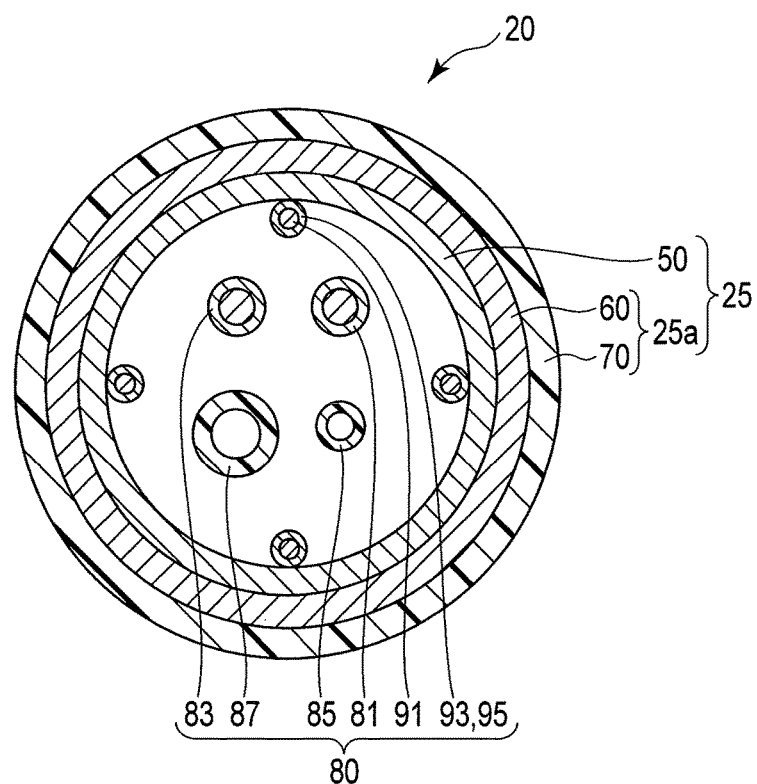
FIG. 6 shows that the built-in densely wound member also serves as a wire insertion member.

As shown in FIG. 6, the built-in densely wound member 95 may be designed to function as a wire insertion member 93. In this case, the bending wire 91 for bending the bendable portion 23 upward (in the U direction) is desirably inserted through the wire insertion member 93 for which the supplement area portion 57 is arranged. With this structure, the filling rate of the interior of the spiral tube 50 is not increased, and the structure of the spiral tube 50 need not be modified. Accordingly, the interior of the spiral tube 50 can be space saving. In addition, the diameter of the spiral tube 50 does not have to be increased. In general, in many cases, the operator bends the bendable portion 23 upward. Therefore, the elasticity of the flexible tube 25 can be supplemented with respect to the direction in which the bendable portion 23 is bent. As a result, the insertion-removal property of the flexible tube 25 can be enhanced. The present embodiment can provide a flexible tube 25 whose elasticity is supplemented in a direction desired by the operator.

The spiral tube 50 may be provided with a stop member (not shown) for preventing the built-in densely wound member 95 from being shifted in a radial direction of the spiral tube 50 or in a circumferential direction thereof.

Second Embodiment

According to the first embodiment, the built-in densely wound member 95 in the first supplement area portion 57a and the built-in densely wound member 95 in the second supplement area portion 57b are integrally formed of the same linear member 95a and constitute one member. The second embodiment differs from the first embodiment in this point.

Figure 7A:
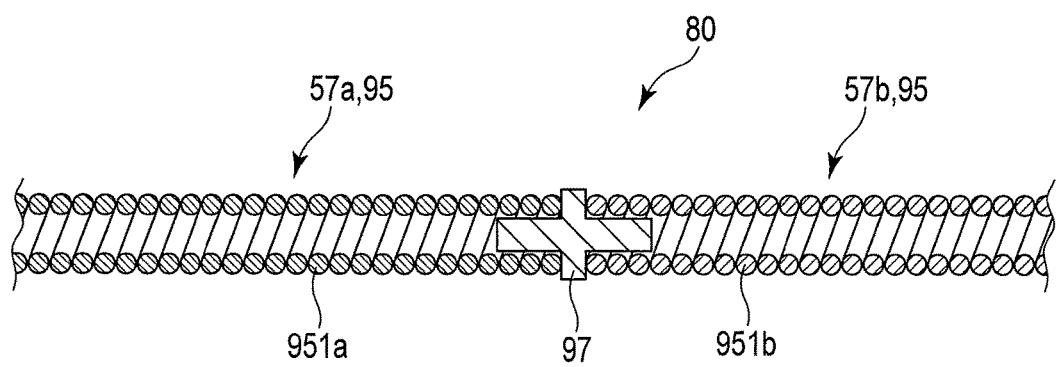
FIG. 7A illustrates the structure of a built-in densely wound member of the second embodiment.

As shown in FIG. 7A, the built-in densely wound member 95 in the first supplement area portion 57a and the built-in densely wound member 95 in the second supplement area portion 57b constitute different members. In this case, for example, the linear member 951a with which to form the former built-in densely wound member 95 and the linear member 951b with which to form the latter built-in densely wound member 95 are different members. That is, the material of linear member 951a and the material of linear member 951b are different.

A proximal end portion of the former densely wound member 95 and a distal end portion of the latter densely wound member 95 are connected to each other by means of a connector member 97. The connector member 97 is, for example, a rod-like member with metallic plating or a rod-like member formed of metal. The connector member 97 is, for example, a metallic joint. The proximal end portion of the former built-in densely wound member 95 is connected to the connector member 97, for example, by laser welding or brazing. The distal end portion of the latter built-in densely wound member 95 is connected to the connector member 97 in a similar method. The connector member 97 is formed of a material different from the materials of the linear members 951a and 951b. The connector member 97 has such a shape as prevents wax from remaining inside the built-in densely wound member 95.

The initial tension A of linear member 951a is higher than the initial tension B of linear member 951b. Linear members 951a and 951b have the same longitudinal sectional shape and the same diameter.

In the second embodiment, the built-in densely wound member 95 in the first supplement area portion 57a and the built-in densely wound member 95 in the second supplement area portion 57b constitute different members. With this structure, the built-in densely wound members 95 under different initial tensions can be easily manufactured.

A description will now be given of modifications of the second embodiment.

[First Modification]

As shown in FIG. 7B, linear members 951a and 951b have different longitudinal sectional shapes and different diameters. The longitudinal sectional shape of linear member 951a is, for example, rectangular, while the longitudinal sectional shape of linear member 951b is, for example, circular.

With this feature, the first modification is advantageous in that the first supplement area portion 57a and the second supplement area portion 57b can be easily distinguished from each other when the built-in densely wound member 95 is manufactured.

[Second Modification]

As shown in FIG. 7C, linear members 951a and 951b have the same longitudinal sectional shape (e.g., circular)

but have different wire diameters. The wire diameter of linear member 951*a* is larger than that of linear member 951*b*.

With this feature, the second modification is advantageous in that the first supplement area portion 57*a* and the second supplement area portion 57*b* can be easily distinguished from each other when the built-in densely wound member 95 is manufactured.

[Third Modification]

As shown in FIG. 7D, a linear member 95*c* may be inserted through the built-in densely wound member 95. The linear member 95*c* is, for example, a glass fiber of an illumination unit or an electric cable of an imaging unit. In this case, the connector member 97 is cylindrical, for example.

With this structure, the third modification is advantageous in that the filling rate of the interior of the spiral tube 50 need not be increased, and the structure of the flexible tube 25 need not be modified. Accordingly, the interior of the spiral tube 50 can be space saving.

Third Embodiment

Figure 8:
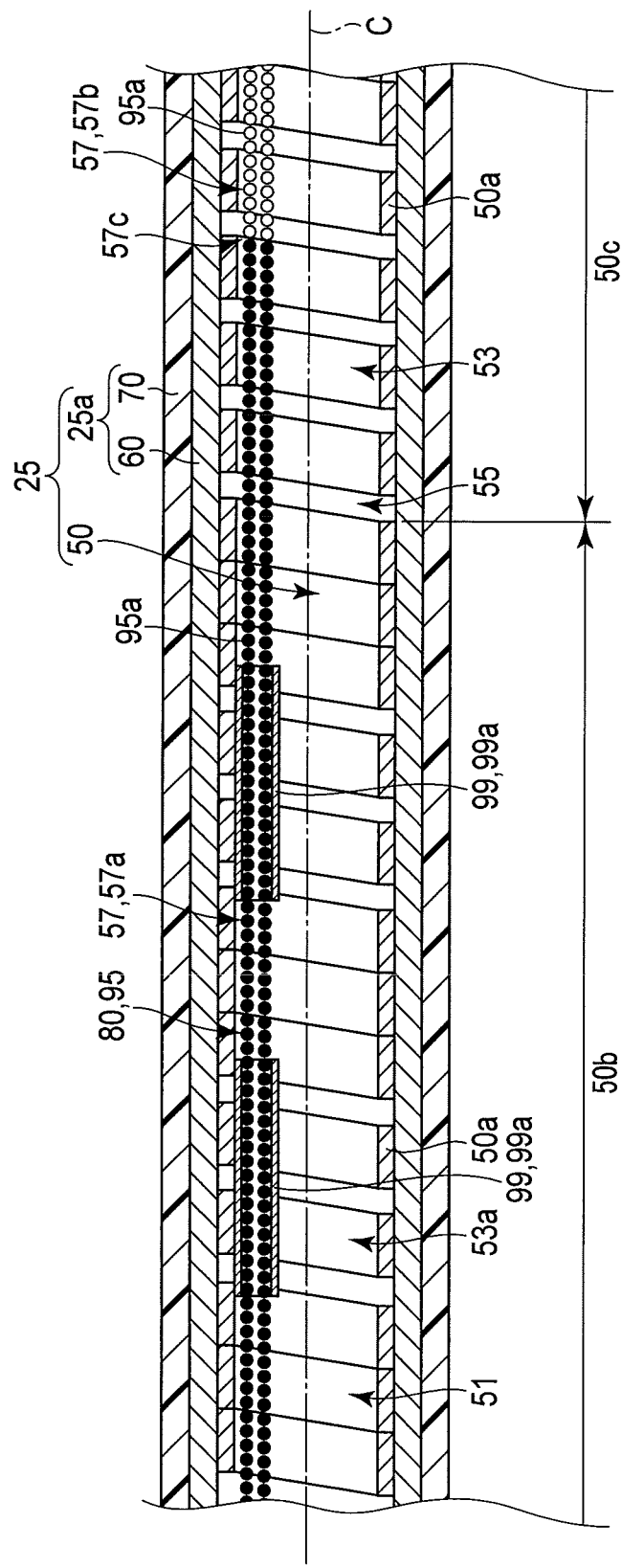
FIG. 8 illustrates the structure of a built-in densely wound member of the third embodiment.

As shown in FIG. 8, the built-in densely wound member 95 further includes a supplement member 99 as a member different from the built-in densely wound member 95. The supplement member 99 includes a supplement area portion 99*a* different from the supplement area portion 57 of the built-in densely wound member 95. The supplement area portion 99*a* may be provided along the overall length of the supplement member 99. The supplement member 99 is arranged in the built-in densely wound member 95 such that the supplement member 99 is covered at least with the loosely wound portion 53 of the first area portion 50*b*. The supplement member 99 may be arranged in the built-in densely wound member 95 such that the supplement member 99 is covered with the first area portion 50*b* along the overall length thereof. The supplement member 99 is tubular shape and has a cylindrical shape, for example. The built-in densely wound member 95 is inserted into the supplement member 99 such that an inner circumferential surface of the supplement member 99 is in contact with an outer circumferential surface of the built-in densely wound member 95. As can be seen from this, the supplement member 99 covers part of the built-in densely wound member 95. For example, the initial tension of the supplement area portion 99*a* may be equal to the initial tension of the densely wound portion 51, or may be different therefrom. For example, the initial tension of the supplement area portion 99*a* may be equal to the initial tension A of the first supplement area portion 57*a*, or may be different therefrom. For example, the initial tension of the supplement area portion 99*a* may be equal to the initial tension B of the second supplement area portion 57*b*, or may be different therefrom.

For example, the supplement member 99 includes at least one of an elastic tube having predetermined elasticity, a heat shrinkable tube, a resin tape, a resin cylindrical member, a spring member and a coil member.

In the third embodiment, the elasticity of the flexible tube 25 can be further supplemented by the supplement member 99. Since the supplement area portion 99*a* is provided in the third embodiment, it is not necessary to increase the plate thickness of the spiral thin plate member 50*a* with which to form the spiral tube 50.

The third embodiment can therefore provide a flexible tube 25 in which the supplement member 99 under an initial tension ensures desirable elasticity and insertion-removal property. Since the flexible tube 25 of the third embodiment easily maintains the straight state and can be easily inserted into the body cavity, the insertion-removal property of the flexible tube 25 can be further enhanced. In the third embodiment, the distal end portion of the flexible tube 25 can be further reliably twisted in accordance with the twisting motion applied to the proximal end portion of the flexible tube 25. When the proximal end portion of the flexible tube 25 is twisted, the twisting force is reliably transmitted to the distal end portion of the flexible tube 25, and the distal end portion of the flexible tube 25 can be reliably twisted in response to the twisting motion applied to the proximal end portion of the flexible tube 25.

The supplement member 99 is covered, for example, with the loosely wound portion 53*a* arranged in the first area portion 50*b*. Because of the positional relationship between the densely wound portion 51 and the supplement area portion 57 and the positional relationship between the supplement member 99 and the loosely wound portion 53*a*, the elasticity of the distal end portion of the flexible tube 25 is substantially uniform along the overall length of the distal end portion.

Fourth Embodiment

As shown in FIGS. 9A, 9B and 9C, a plurality of built-in densely wound members 95 are arranged. In the direction around the central axis C of the spiral tube 50, the built-in densely wound members 95 are arranged at equal intervals. As shown in FIG. 9A, the built-in densely wound members 95 are away from each other, for example, by 180°. As shown in FIG. 9B, the built-in densely wound members 95 are away from each other, for example, by 120°. As shown in FIG. 9C, the built-in densely wound members 95 are away from each other, for example, by 90°.

For easy understanding, illustration of part of the built-in components 80 (e.g., an illumination cable 81) is omitted in FIGS. 9A, 9B and 9C.

According to the present embodiment, when the flexible tube 25 is bent, the bending easiness/bending hardness of the flexible tube 25 is not very different without reference to directions in which the built-in densely wound members 95 are provided. Accordingly, the flexible tube 25 can be easy to handle.

The present invention is not limited to the above-described embodiments, and can be embodied by modifying the structures without departing from the gist of the invention. Various inventions can be made by properly combining the structure elements disclosed in connection with the above embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube for use in an insertion device, the flexible tube comprising:
   a spiral tube having elasticity and including (i) a first area portion which includes an area under an initial tension at a portion along a central axis of the spiral tube, and (ii) a second area portion which is continuous with a proximal end side of the first area portion and which is not under the initial tension; and a built-in component disposed within and extending through the spiral tube, the built-in component including at least one coil which is located in the spiral tube and supplements the elasticity of the spiral tube, the built-in component including (i) a first supplement area portion under an initial tension, and (ii) a second supplement area portion which is under an initial tension smaller than the initial tension of the first supplement area portion, the second supplement area portion being located on a more proximal end side than the first supplement area portion, wherein:

the first supplement area portion is arranged in a first area portion side of the spiral tube, and the second supplement area portion is arranged in a second area portion side of the spiral tube, and a boundary portion between the first supplement area portion and the second supplement area portion is positioned at a position which is shifted, in a direction of the central axis of the spiral tube, from a position where the first area portion and the second area portion are continuous with each other.

2. The flexible tube according to claim 1, wherein the boundary portion is located inside the second area portion.

3. The flexible tube according to claim 2, wherein
the first supplement area portion is covered with entirety of the first area portion and a distal end portion of the second area portion in the direction of the central axis, and the second supplement area portion is covered with a proximal end portion side of the second area portion.

4. The flexible tube according to claim 2, wherein, in the boundary portion, the initial tension of the built-in component gradually decreases from the first supplement area portion to the second supplement area portion.

5. The flexible tube according to claim 4, wherein the first supplement area portion is integral with the second supplement area portion.

6. The flexible tube according to claim 4, wherein the first supplement area portion is a different portion from the second supplement area portion.

7. The flexible tube according to claim 1, wherein the at least one coil includes a plurality of coils arranged at equal intervals in a circumferential direction around the central axis of the spiral tube.

8. The flexible tube according to claim 1, wherein
the built-in component further includes a wire insertion member through which a bending wire configured to bend a bendable portion of the insertion device is inserted, and the at least one coil is a different member from the wire insertion member.

9. An insertion device comprising:
an insertion portion which includes the flexible tube according to claim 1, the insertion portion being configured to be inserted into a lumen; and an operation portion which is coupled to a proximal end portion of the insertion portion, the operation portion being configured to operate the insertion device.

10. The flexible tube according to claim 1, wherein
the first area portion includes (i) a densely wound portion which is under the initial tension of the first area portion, and (ii) a loosely wound portion which is continuous with at least one end of the densely wound portion and which is not under the initial tension of the first area portion, and the densely wound portion and the loosely wound portion are alternately arranged in the direction of the central axis.

11. The flexible tube according to claim 1, further comprising:
a flexible envelope which includes at least one layer arranged in a radial direction of the flexible tube and which covers the spiral tube, wherein the spiral tube provides the elasticity in cooperation with the envelope.

* * * * *